(12) United States Patent
Aoki

(10) Patent No.: US 8,731,804 B2
(45) Date of Patent: May 20, 2014

(54) HYDROGEN DETECTING DEVICE AND METHOD, AND INTERNAL COMBUSTION ENGINE ABNORMALITY DECIDING DEVICE

(75) Inventor: Keiichiro Aoki, Numazu (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 1119 days.

(21) Appl. No.: 12/668,467

(22) PCT Filed: Jul. 9, 2008

(86) PCT No.: PCT/JP2008/062772
§ 371 (c)(1),
(2), (4) Date: Jan. 11, 2010

(87) PCT Pub. No.: WO2009/008540
PCT Pub. Date: Jan. 15, 2009

(65) Prior Publication Data
US 2010/0191444 A1    Jul. 29, 2010

(30) Foreign Application Priority Data
Jul. 9, 2007   (JP) ................................ 2007-180283

(51) Int. Cl.
*B60T 7/12*     (2006.01)
*G05D 1/00*     (2006.01)
*G06F 7/00*     (2006.01)
*G06F 17/00*    (2006.01)
*F01N 1/00*     (2006.01)

(52) U.S. Cl.
USPC ........................................... 701/109; 60/272

(58) Field of Classification Search
USPC ........... 60/274, 276, 277, 285, 286; 73/23.31, 73/23.32, 114.71, 114.72, 114.73, 114.75; 123/674, 679, 681, 690, 694, 695; 204/424, 425, 426, 431; 701/103, 109, 701/114
See application file for complete search history.

(56) References Cited

U.S. PATENT DOCUMENTS

| | | | |
|---|---|---|---|
| 6,220,017 B1* | 4/2001 | Tayama et al. | 60/277 |
| 7,926,330 B2* | 4/2011 | Huang et al. | 73/114.38 |
| 2005/0056266 A1* | 3/2005 | Ikemoto et al. | 123/688 |
| 2007/0012086 A1* | 1/2007 | Ikemoto et al. | 73/23.32 |
| 2009/0037079 A1* | 2/2009 | Suzuki et al. | 701/103 |

FOREIGN PATENT DOCUMENTS

| | | |
|---|---|---|
| JP | 8 49585 | 2/1996 |
| JP | 11 247687 | 9/1999 |
| JP | 2000 8920 | 1/2000 |

(Continued)

*Primary Examiner* — Stephen K Cronin
*Assistant Examiner* — Sizo Vilakazi
(74) *Attorney, Agent, or Firm* — Oblon, Spivak, McClelland, Maier & Neustadt, L.L.P.

(57) ABSTRACT

A device, which detects information about a hydrogen concentration level, includes an air-fuel ratio sensor, an air-fuel ratio controller, and a detecting portion. The detecting portion calculates either a ratio of response periods or a difference between the response periods to detect the hydrogen concentration level. One of the response periods is a period from the time the air-fuel ratio controller switches the target air-fuel ratio from rich to lean to the time the air-fuel ratio sensor detects this. The other of the response periods is a period from the time the air-fuel ratio controller switches the target air-fuel ratio from lean to rich to the time the air-fuel ratio sensor detects this. This allows the decisions of a variation between cylinders and an exhaust purifying catalyst degradation.

1 Claim, 21 Drawing Sheets

(56) References Cited

FOREIGN PATENT DOCUMENTS

| | | |
|---|---|---|
| JP | 2001 124730 | 5/2001 |
| JP | 2003 120383 | 4/2003 |
| JP | 2005 121003 | 5/2005 |
| JP | 2006 152845 | 6/2006 |
| JP | 2006 291893 | 10/2006 |
| JP | 2007 154840 | 6/2007 |

* cited by examiner

THEORETICAL AIR-FUEL RATIO

| COMPO-NENT | SELF-DIFFUSION COEFFICIENT D11(TEMPER-ATURE: 800 DEGREES C) | MUTUAL-DIFFUSION COEFFICIENT D11(TEMPER-ATURE: 800 DEGREES C) (MEDIUM GAS: AIR) | D12 RATIO ($O_2=1$ REFERENCE) |
|---|---|---|---|
| $O_2$ | 1.80 | 1.77 | 1 |
| CO | 1.76 | 1.75 | 0.99 |
| $H_2$ | 12.20 | 6.44 | 3.64 |
| $CH_4$ | 2.07 | 1.96 | 1.11 |
| $C_2H_6$ | 1.34 | 1.02 | 0.59 |
| $C_3H_8$ | 0.63 | 1.05 | 0.59 |

US 8,731,804 B2

HYDROGEN DETECTING DEVICE AND METHOD, AND INTERNAL COMBUSTION ENGINE ABNORMALITY DECIDING DEVICE

TECHNICAL FIELD

The present invention relates to a hydrogen detecting device that detects information about hydrogen concentration level and a method thereof, and an internal combustion engine abnormality deciding device that decides whether there is an abnormality of an internal combustion engine on the basis of information about the hydrogen concentration level detected by the hydrogen detecting device.

BACKGROUND ART

It is known that outputs of an air-fuel ratio sensor are different from one another when hydrogen exists in a gas to be detected. Patent Document 1 discloses that the detection of switching from rich air-fuel ratio to lean air-fuel ratio is delayed in case where the hydrogen exists.

Patent Document 2 discloses that the output of the air-fuel ratio sensor tends to be richer under the influence of a rich gas containing hydrogen.

Patent Document 1: Japanese Unexamined Patent Publication No. 11-247687
Patent Document 2: Japanese Unexamined Patent Publication No. 2006-291893
Patent Document 3: Japanese Unexamined Patent Publication No. 8-49585
Patent Document 4: Japanese Unexamined Patent Publication No. 2006-152845
Patent Document 5: Japanese Unexamined Patent Publication No. 2003-120383

DISCLOSURE OF THE INVENTION

Problems to be Solved by the Invention

However, it is not possible to calculate the hydrogen concentration level or the hydrogen concentration on the basis of the techniques disclosed in Patent Document 1 or 2.

The present invention has been made in view of the above circumstances and has an object to provide a device for detecting information about a hydrogen concentration level and a method thereof, by use of a sensor detecting an oxygen concentration at low cost. Also, the present invention has an object to provide a device for detecting the information about the hydrogen concentration level by use of the sensor detecting the oxygen concentration at low cost and deciding whether there is an abnormality of an internal combustion engine.

Means for Solving the Problems

According to an aspect of the present invention, there is provided a hydrogen detecting device characterized by including: a sensor detecting an oxygen concentration of a gas to be detected; an oxygen concentration controller controlling the oxygen concentration of the gas, to be detected, flowed into the sensor; and a detecting portion detecting information about a hydrogen concentration level on a basis of a low oxygen concentration response period and a high oxygen concentration response period, the low oxygen concentration response period being a response period from a time the oxygen concentration controller switches the oxygen concentration from a high concentration oxygen gas supply to a low concentration oxygen gas supply with respect to a reference oxygen concentration gas to a time an output of the sensor is reflected by the switching, the high oxygen concentration response period being a response period from a time the oxygen concentration controller switches the oxygen concentration from a low concentration oxygen gas supply to a high concentration oxygen gas supply with respect to a reference oxygen concentration gas to a time an output of the sensor is reflected by the switching. With the above configuration, the information about the hydrogen concentration level can be detected by use of the oxygen concentration controller and the sensor.

In the above configuration, the gas to be detected may be an exhaust gas exhausted from an internal combustion engine, the oxygen concentration controller may be an air-fuel ratio controller controlling a target air-fuel ratio, the low oxygen concentration response period may be a response period from a time the air-fuel ratio controller switches the target air-fuel ratio from a lean air-fuel ratio to a rich air-fuel ratio to a time an output of the sensor is reflected by the switching, and the high oxygen concentration response period may be a response period from a time the air-fuel ratio controller switches the target air-fuel ratio from a rich air-fuel ratio to a lean air-fuel ratio to a time an output of the sensor is reflected by the switching. With the above configuration, the information about the hydrogen concentration level can be detected by use of the air-fuel ratio controller and the sensor.

In the above configuration, the detecting portion may detect the information about the hydrogen concentration level on a basis of one of a ratio of the high oxygen concentration response period to the low oxygen concentration response period and a difference between the high and low oxygen concentration response periods.

In the above configuration, the sensor may include: an outside electrode exposed to the gas to be detected; an inside electrode exposed to atmosphere; and an oxygen ion conductive electrolyte arranged between the outside and inside electrodes. The information about the hydrogen concentration level can be detected by use of this sensor.

According to another aspect of the present invention, there is provided an internal combustion engine abnormality deciding device characterized by including: the hydrogen detecting device mentioned above, the gas to be detected being an exhaust gas exhausted from an internal combustion engine; and an abnormality deciding portion deciding an abnormality of the internal combustion engine on a basis of the hydrogen concentration level detected by the detecting portion. With the above configuration, the hydrogen concentration level can be detected by use of the oxygen concentration controller and the sensor, and the abnormality of the internal combustion engine can be decided on the basis of the hydrogen concentration level.

In the above configuration, the internal combustion engine may include a plurality of cylinders; and the abnormality deciding portion may decide that there is a variation between the cylinders, when the hydrogen concentration level detected by the hydrogen detecting device is greater than or equal to a given value. With the above configuration, the variation between the cylinders can be decided.

In the above configuration, the sensor may detect the oxygen concentration of the exhaust gas in a gathering portion of a plurality of exhaust pipes respectively connected to the plurality of cylinders, or the oxygen concentration of the exhaust gas in a downstream of the gathering portion.

In the above configuration, the sensor may detect the oxygen concentration of the exhaust gas in a downstream of an exhaust purifying catalyst; and the abnormality deciding portion may decide that the exhaust purifying catalyst is degraded, when the hydrogen concentration level detected by the hydrogen detecting device is greater than or equal to a given value.

According to another aspect of the invention, there is provided a hydrogen detecting method characterized by including: a step of obtaining a low oxygen concentration response period being a response period from a time an oxygen concentration of a gas, to be detected, flowed into a sensor for detecting an oxygen concentration, is switched from high concentration to low concentration with respect to a reference oxygen concentration to a time an output of the sensor is reflected by the switching; a step of obtaining a high oxygen concentration response period being a response period from a time an oxygen concentration of the gas, to be detected, flowed into the sensor, is switched from low concentration to high concentration with respect to the reference oxygen concentration to a time an output of the sensor is reflected by the switching; and a step of detecting information about a hydrogen concentration level on a basis of the high and low oxygen concentration response periods. With the above configuration, the information about the hydrogen concentration level can be detected.

Effects of the Invention

According to the present invention, there is provided a device for detecting information about a hydrogen concentration level, and a method thereof, by use of a sensor detecting an oxygen concentration at low cost, and a device for detecting the information about a hydrogen concentration level by use of a sensor detecting an oxygen concentration at low cost and deciding whether there is an abnormality of an internal combustion engine.

BEST MODES FOR CARRYING OUT THE INVENTION

Figure 1:
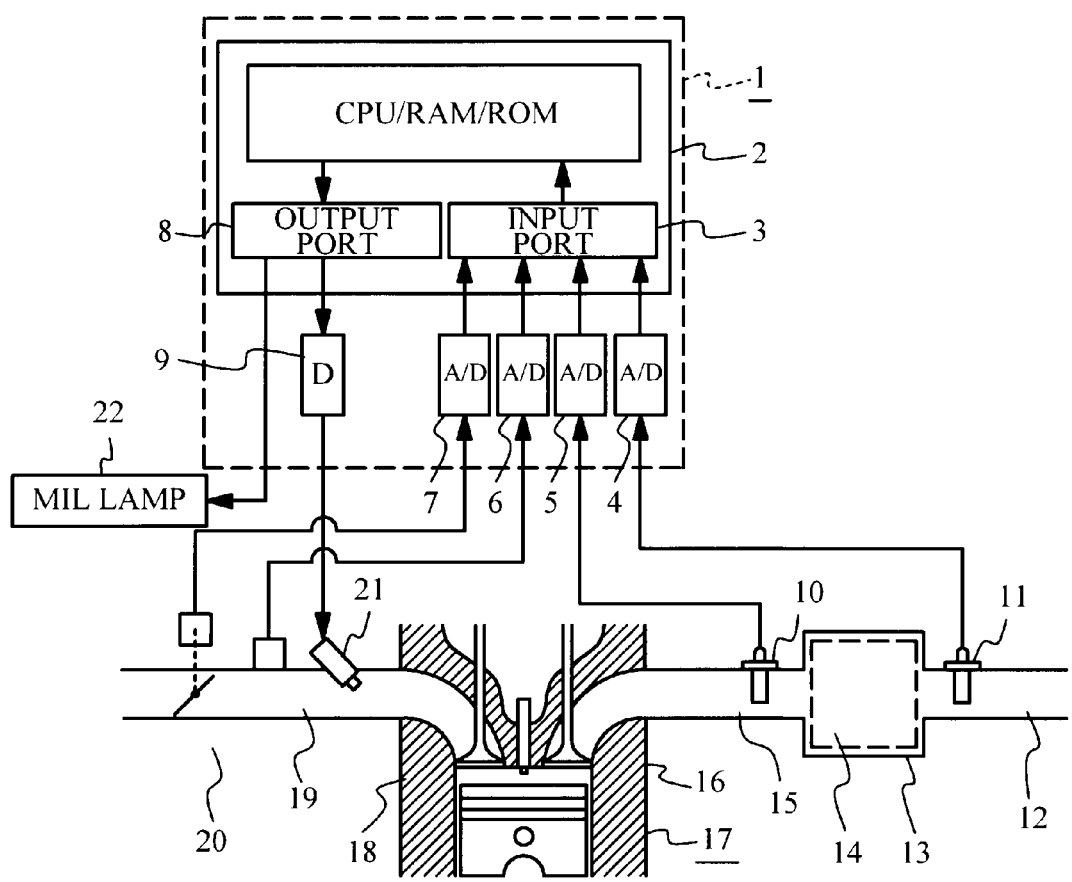
FIG. 1 is a schematic side view of an internal combustion engine.

In the following, a description will be given of the embodiments according to the present invention with reference to the drawings. Like components in each figure are designated with the same reference numerals to simplify or omit the description.

[First Embodiment]

A description will be given, in following order, of a hydrogen detecting device, which is mounted in an internal combustion engine according to the present invention.

1. Basic configurations of the internal combustion engine
2. Principle of an air-fuel ratio sensor
3. Response of the air-fuel ratio sensor to switching of the air-fuel ratio from rich to lean
4. Response of the air-fuel ratio sensor to switching of the air fuel ratio from lean to rich
5. Principle of the hydrogen detecting device which is constructed by combining the air-fuel ratio sensor and an air-fuel ratio controller
6. Flowchart of detecting hydrogen concentration level
7. Another aspect of the present embodiment
8. Effects of the present embodiment

1. Basic Configurations of the Internal Combustion Engine

Figure 2:
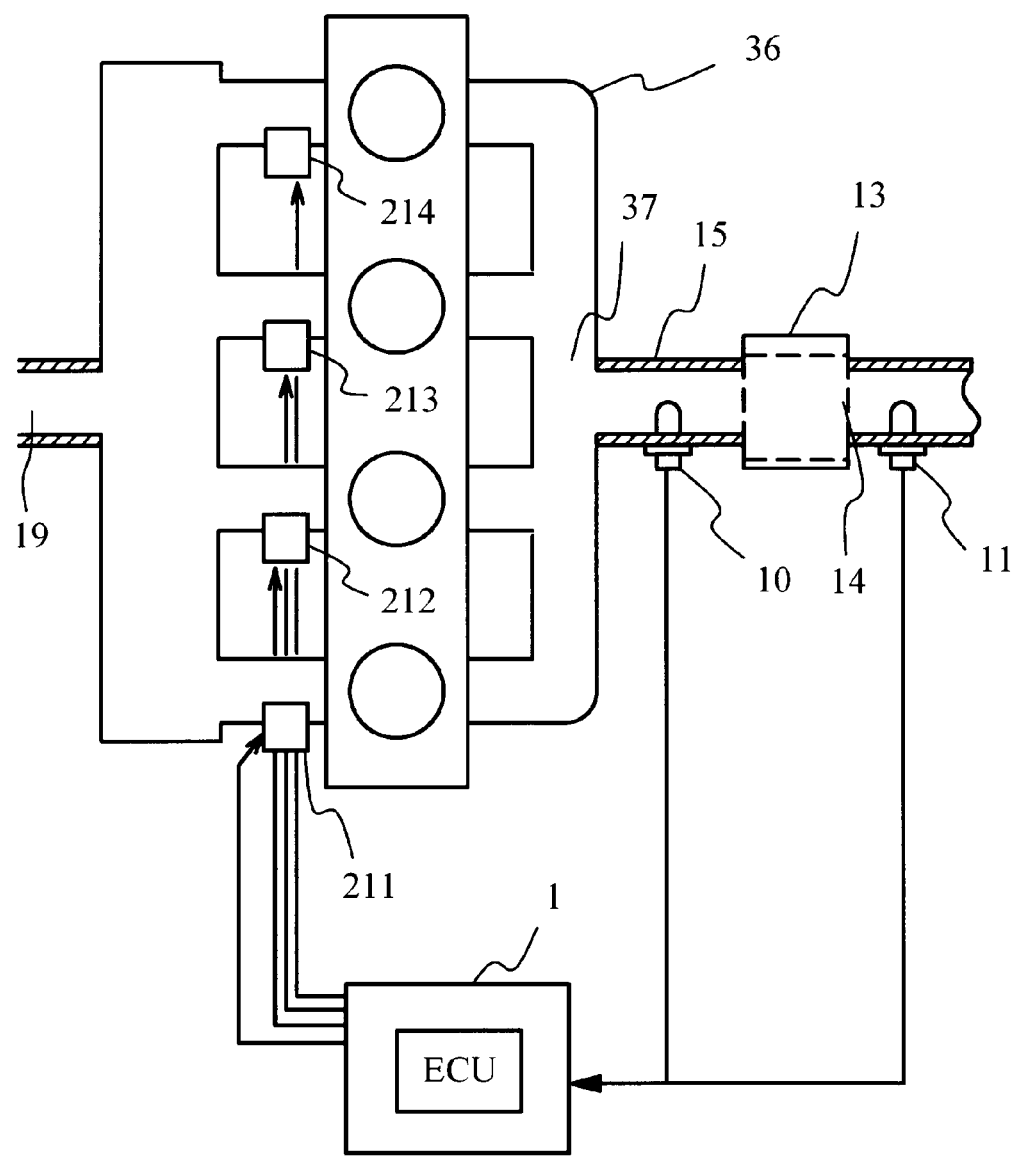
FIG. 2 is a schematic view of a whole configuration of the internal combustion engine viewed from its upper side.

FIGS. 1 and 2 are schematic views for describing the basic configurations according to the first embodiment. FIG. 1 is a schematic side view of the internal combustion engine, and illustrates a cross section of a cylinder, an intake pipe 19 and an exhaust pipe 15 respectively arranged to and from the cylinder, and exhaust gas passing through the exhaust pipe 15. FIG. 2 is a schematic view of the same internal combustion engine viewed from its upper side. FIG. 2 illustrates the common intake pipe 19 and exhaust pipe 15 illustrated in FIG. 1 and the internal combustion engine having plural cylinders. Intake branching pipes are respectively connected to intake ports of the internal combustion engine. Fuel injection valves (211, 212, 213, and 214) are respectively provided in the branching intake pipes. FIG. 1 illustrates the injection valve 21 instead of illustrating the plural fuel injection valves. In addition, the intake branching pipes are connected to a common surge tank (not illustrated). An airflow meter 23 for detecting the intake pressure and a throttle sensor 24 are arranged in the upstream of the surge tank. A common exhaust manifold 36 is connected to exhaust ports of each cylinder of the internal combustion engine. The exhaust manifold 36 has a gathering portion 37 of the exhaust pipe. A catalytic converter 13 in which an exhaust purifying catalyst 14 is installed is provided in the exhaust pipe 15. A muffler (not illustrated) is provided at the exhaust pipe 12 in the downstream of the catalytic converter 13. Air-fuel sensors are provided in the upstream and downstream of an exhaust purifying catalyst. An upstream side air-fuel ratio sensor 10 is provided in the upstream of the catalytic converter 13, and a downstream side air-fuel ratio sensor 11 is provided in the downstream of the catalytic converter 13. The upstream side air-fuel ratio sensor 10 or the downstream side air-fuel ratio sensor 11 corresponds to a sensor for detecting the oxygen concentration of the gas to be detected.

This internal combustion engine includes a control system and an Electronic Control Unit (ECU) 1. The ECU1 includes a microcomputer 2. The microcomputer 2 is configured with known logic circuits including a CPU, a RAM, a ROM, an A/D converter, an I/O port. An input port of the microcomputer is connected through the A/D converter to the upstream side air-fuel ratio sensor 10, the downstream side air-fuel ratio sensor 11, the airflow meter 23, and the throttle sensor 24. The ECU 1 takes in obtains detected electrical signals (analog signals) through the A/D converter, and calculates an A/F value and an element impedance Zac as necessary. Further, an output port of the microcomputer is connected to the injection valve 21 through a driving circuit. Furthermore, the output port is connected to an MIL lamp 22. When the abnormality is caused in the internal combustion engine, the MIL lamp 22 turns on to inform the driver of the abnormality. The ECU 1 corresponds to the basic configuration according to the present invention by means of software, and executes processes of a flowchart, to be mentioned later, in accordance with programs stored in ROM.

The ECU 1 performs a calculation by use of an input signal of each sensor, decides an injection quantity (injection time) on the basis of the detected intake air quantity and the target air-fuel ratio, and controls the fuel injection valves. Thus, the fuel injection valve 21 injects a given quantity of fuel. The ECU 1 deciding the target air-fuel ratio corresponds to the air-fuel ratio controller or the oxygen concentration controller. The ECU 1 corresponds to the air-fuel ratio controller or the oxygen concentration controller and the detecting portion described in claims. The ECU 1 and the upstream side air-fuel ratio sensor 10 or the ECU 1 and the downstream side air-fuel ratio sensor 11 correspond to the hydrogen detecting device.

The air-fuel ratio feedback control will be described. The ECU 1 decides to which side the air-fuel ratio of the exhaust gas is fluctuated, rich side or lean side, with respect to the theoretical air-fuel ratio, on the basis of the detection result of the upstream side air-fuel ratio sensor 10 or the downstream side air-fuel ratio sensor 11. The air-fuel ratio controller corrects the target air-fuel ratio to be opposite side of this fluctuation, and adjusts the target air-fuel ratio such that a factual air-fuel ratio comes closer to the theoretical air-fuel ratio. For example, this is particularly described in Japanese Unexamined Patent Application Publication No. 8-49585. In the present embodiment, with the use of the air-fuel ratio sensor and the air-fuel ratio controller which are used in the air-fuel ratio feedback control, it is made possible for the hydrogen detecting device having a characteristic control to detect the information about the hydrogen concentration level. Thus, it is unnecessary to add a new hard configuration such as a new sensor, whereby it is possible to detect the information about the hydrogen concentration level at low cost.

Figure 7:
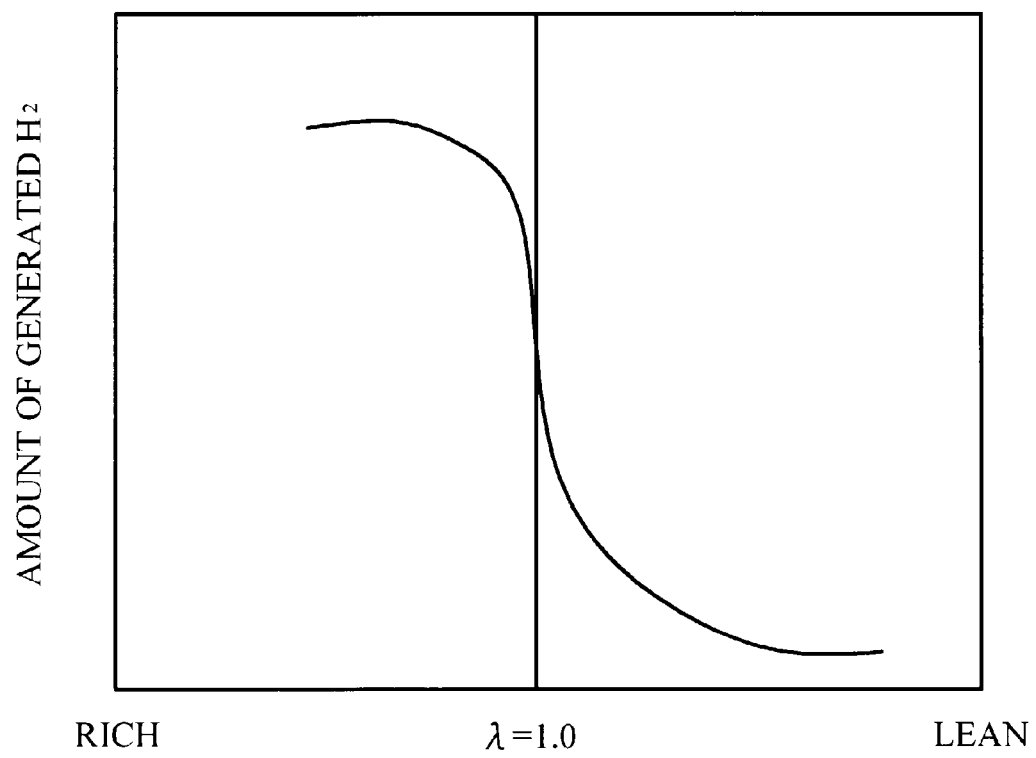
FIG. 7 is a view of the amount of hydrogen generated by combustion in a case where the target air-fuel ratio is rich and in a case where the target air-fuel ratio is lean.

Here, the components of the exhaust gas will be described, in a case where the air-fuel ratio of air-fuel mixture generated in a combustion chamber is rich, and in a case where the air-fuel ratio is lean, separately. When the air-fuel ratio is rich, a larger amount of fuel is injected than that of the theoretical air-fuel ratio. Therefore, unburned hydrocarbon HC, water $H_2O$, carbon monoxide CO and the like are generated in the combustion chamber after the combustion. As will be described later in detail, these components are reacted by the water-gas-shift reaction and the steam reforming within the exhaust pipe, thereby generating hydrogen $H_2$, methane $CH_4$, carbonic anhydride $CO_2$ and the like. As illustrated in FIG. 7, when the air-fuel ratio is rich, the concentration of hydrogen $H_2$ in the exhaust gas is higher than the case where the air-fuel ratio is lean.

On the other hand, when the air-fuel ratio is lean, the fuel is almost used by combustion and oxygen $O_2$ remains in the combustion chamber after the combustion. When the air-fuel ratio is lean, the concentration of oxygen in the exhaust gas is higher than the case where the air-fuel ratio is the theoretical air-fuel ratio.

2. Principle of the Air-Fuel Ratio Sensor

Figure 3:
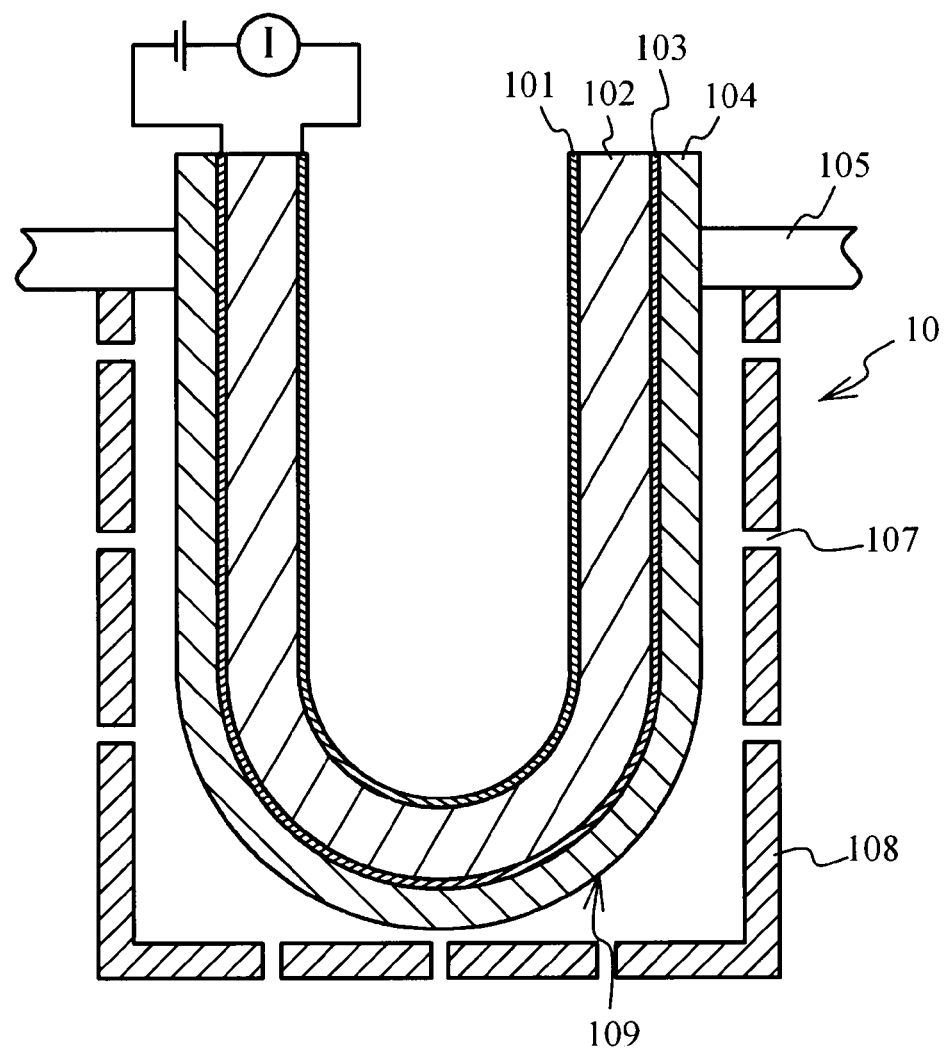
FIG. 3 is a schematic view of an air-fuel ratio sensor in which a sensor element is illustrated at its center.

Here, a description will be given of the air-fuel ratio sensor employed as the upstream side air-fuel ratio sensor 10 or the downstream side air-fuel ratio sensor 11. The air-fuel ratio sensor detects the oxygen concentration of the gas to be detected, on the basis of an oxygen partial pressure. FIG. 3 is a schematic view for describing the air-fuel ratio sensor. As illustrated in FIG. 3, the air-fuel ratio sensor includes a cover 108. The cover 108 is attached to be exposed to the exhaust gas. The cover 108 is provided with plural air holes 107 for introducing the exhaust gas into the cover 108. The minimum flow velocity of the exhaust gas in the exhaust pipe is about 1 m/s to about 2 m/s. These air holes 107 are provided such that the flow velocity of the introduced exhaust gas decreases to one-tenths. The air holes 107 make the pressure of the exhaust gas in the cover substantially identical to the atmosphere pressure.

A sensor element 109 is arranged within the cover. The sensor element 109 has a tube structure with a closed end. The outer surface of the tube structure is covered with a porous layer 104 providing a diffuse resistive layer. The porous layer is constructed with ceramics of, for example, a spinel-type compound ($MgO.Al_2O_3$) using alumina. In the porous layer, gas permeability (porosity) is defined. The porosity is defined such that the volume of the space in the porous layer is divided by the volume of the whole porous layer.

An outside electrode 103 is provided at the inner side of the porous layer 104. That is to say, the porous layer 104 is provided at the outer surface of the outside electrode. A catalyst or a coating layer may be provided separately, at the outside of the porous layer 104. The outside electrode 103 is exposed to the exhaust gas passing through the porous layer 104. An oxygen ion conductive solid electrolyte 102 as a solid electrolyte is provided at the further inner side of the outside electrode 103. The oxygen ion conductive solid electrolyte 102 includes zirconia. An inside electrode 101 is provided at the inner surface of the oxygen ion conductive solid electrolyte 102. The inside electrode 101 and the outside electrode 103 are made from a metal such as Pt. The inside electrode and outside electrode are connected to a lead wire which extends outwardly through a metallic terminal. The metallic terminal is in pressure contact with the surface of the oxygen ion conductive solid electrolyte 102.

An atmosphere chamber 110 is provided at the inner side of the inside electrode. The atmospheric air is introduced into the atmosphere chamber 110. A heater (not illustrated) may be arranged within the atmosphere chamber 110 to accelerate the activation of the sensor. Additionally, the sensor element 109 is heated to have an activated temperature such as about 700 degrees C., thereby stabilizing its output property.

The operation principle of the air-fuel ratio sensor will be described with reference to FIGS. 4A to 4E. FIGS. 4A to 4E are schematic views of the outside electrode 103, the inside electrode 101, the oxygen ion conductive solid electrolyte 102, and the porous layer 104 which are the characteristic portions of the air-fuel ratio sensor.

The pressure of the exhaust gas applied to the outside electrode is set to be substantially identical to the atmosphere pressure. Therefore, the air-fuel sensor detects the oxygen concentration by use of the current passing through the both electrodes or the voltage, on the basis of the difference in oxygen partial pressure between the outside electrode 103 and the inside electrode 101.

Figure 4A:
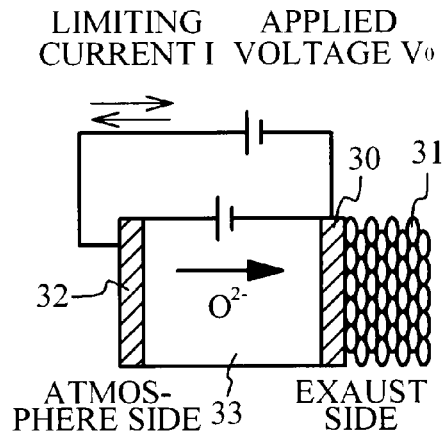
FIGS. 4A to 4E are schematic views of an operation principle of the air-fuel ratio sensor.
Figure 4B:
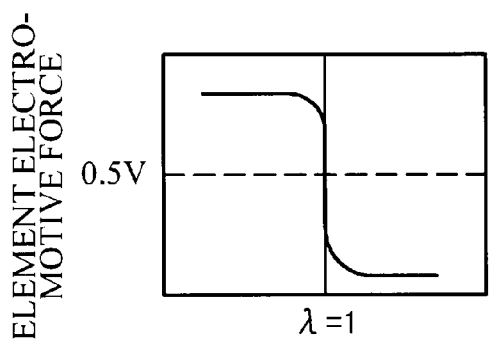
Figure 4C:
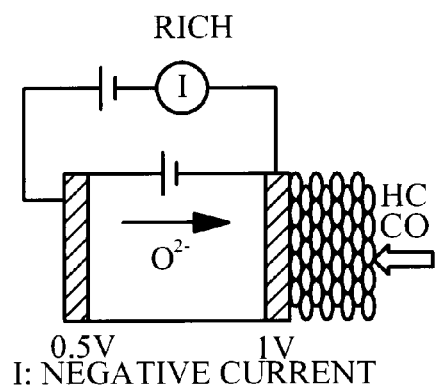
Figure 4D:
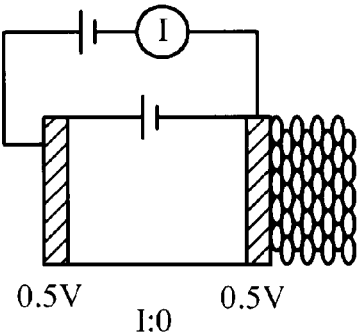
Figure 4E:
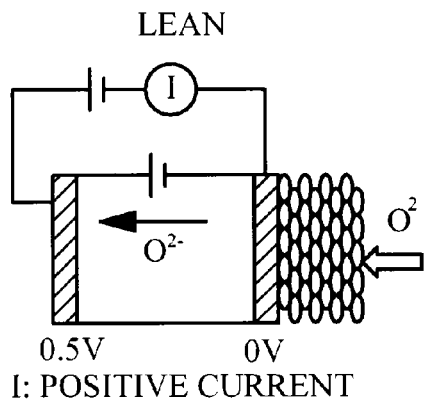

As illustrated in FIGS. 4A to 4E, the voltage V0 is applied between the inside electrode 101 and the outside electrode 103 respectively provided at both surfaces of the oxygen concentration detecting element. The exhaust gas around the sensor element 109 is introduced into the porous layer 104 from its side portion, and reaches the outside electrode 103. When the exhaust gas is rich at this time, unburned component molecule HC, carbon monoxide CO, hydrogen $H_2$ move in the porous layer 104, as illustrated in FIG. 4A. Meanwhile oxygen $O_2$ in the atmosphere chamber is ionized at the inside electrode, and oxygen ion ($O^{2-}$) moves from the inside electrode to the outside electrode in the oxygen ion conductive solid electrolyte. This is because the oxygen partial pressure of the inside electrode 101 located at the atmosphere side is larger than that of the outside electrode 103 located at the exhaust side. Next, oxygen molecule $O_2$ is generated by the electrode reaction of the inside electrode, and is reacted with unburned component molecule HC, carbon monoxide CO, and hydrogen $H_2$ by a catalyzed reaction, so that carbonic anhydride $CO_2$ and water $H_2O$ are generated. In this manner, the element current (minus current) Ip flows from the outside electrode to the inside electrode, thereby producing the electromotive force (1V) in the element. Conversely, when the exhaust gas is lean, oxygen molecule $O_2$ moves in the porous layer, and then develops an electrode reaction of oxygen molecule $O_2$ in the outside electrode 103 to ionize oxygen molecule $O_2$, as illustrated in FIG. 4E. After oxygen ion ($O^{2-}$) moves from the outside electrode 103 toward the inside electrode 101 in the oxygen ion conductive solid electrolyte, oxygen molecule $O_2$ is produced in the inside electrode 101 to be exhausted into the atmosphere chamber 110. In this way, the element current Ip (plus current) flows from the inside electrode to the outside electrode. The electromotive force of the element is 0V. In the theoretical air-fuel ratio, the electromotive force of the element is proportional to the applied voltage, so that the element current Ip is 0.

As described above, oxygen ion ($O^{2-}$) moves in the oxygen ion conductive solid electrolyte, in response to the difference in the oxygen concentration between the both electrodes, that is, the difference in the oxygen partial pressure between the both electrodes. Voltage V0=0.5 V (referring to FIG. 4B) is applied between the both electrodes in the reverse direction, Voltage V0 corresponding to the electromotive force generated in the theoretical air-fuel ratio. In this figure, an air excess ratio ($\lambda$)=1 corresponds to the theoretical air-fuel ratio. This principle allows the detection of the air-fuel ratio on the basis of the element current value flowed between the both electrodes. The electromotive force, of the element, generated between the both electrodes exhibits the so-called Z characteristic in the vicinity of the theoretical air-fuel ratio.

In the present embodiment, the air-fuel ratio sensor is used, on the condition that there is little difference in the pressure between the exhaust gas in the vicinity of the sensor element 109 and the atmosphere is little. This allows the detection of the oxygen concentration of the exhaust gas on the basis of the difference in the oxygen partial pressure between the outside electrode and the inside electrode, as mentioned above. The air-fuel ratio sensor is an A/F sensor detecting the element current Ip or an $O_2$ sensor detecting the electromotive force generated between the electrodes.

Figure 5A:
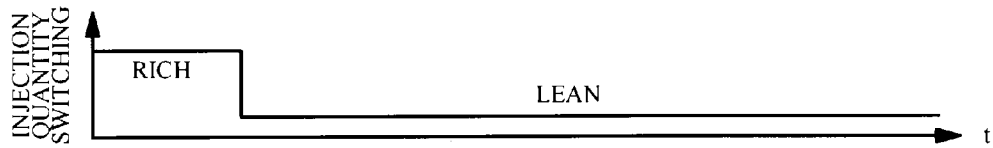
FIGS. 5A to 5C are views for describing time-series changes in the concentration of each component in the vicinity of the outside electrode of the air-fuel ratio sensor and time-series changes in the voltage of an $O_2$ sensor when the air-fuel ratio controller switches the target air-fuel ratio from rich to lean.
Figure 5B:
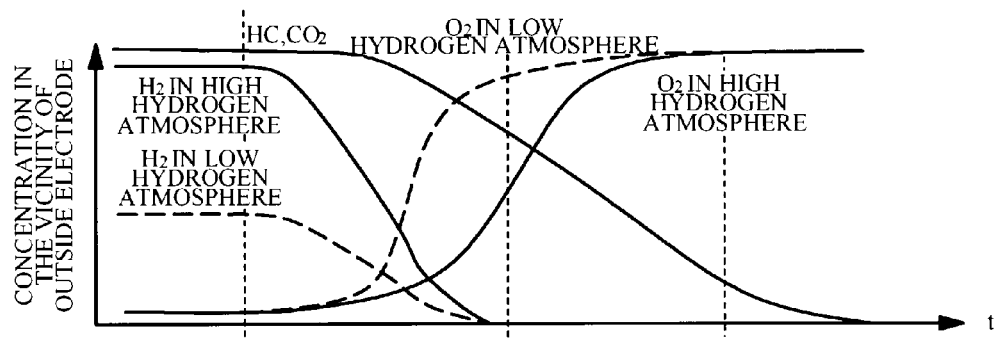
Figure 5C:
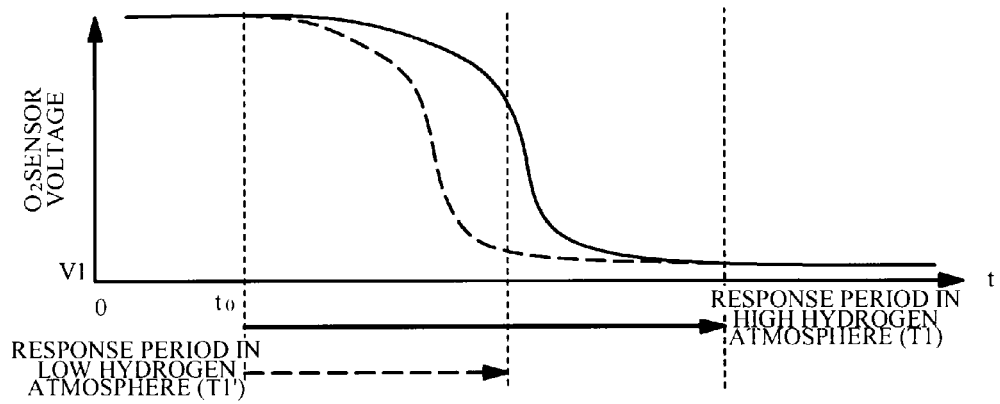

3. Response of the Air-Fuel Ratio Sensor to Switching of the Air-Fuel Ratio from Rich to Lean A description will be given of how the response of the air-fuel ratio sensor changes, with reference to FIGS. 5A to 5C, when the air-fuel ratio controller serving as the oxygen concentration controller switches the target air-fuel ratio from rich to lean, in a case where a large amount of hydrogen is present in the exhaust gas (hereinafter referred to as high hydrogen atmosphere), and in a case where a small amount of hydrogen is present in the exhaust gas (hereinafter referred to as low hydrogen atmosphere). FIG. 5B is a schematic view of concentration distribution of each component within the porous layer 104 and in the vicinity of the outside electrode in time series order. FIG. 5C is a view of time-series changes in the voltage of the electromotive force generated between the both electrodes of the air-fuel ratio sensor. The high hydrogen atmosphere is indicated by solid lines, and the low hydrogen atmosphere is indicated by broken lines.

When the target air-fuel ratio is rich (A/F value 14), hydrogen $H_2$, methane $CH_4$, hydrocarbon HC, and carbon monoxide CO of the exhaust gas are present in the vicinity of the outside electrode of the air-fuel ratio sensor. This state is indicated by t<$t_0$, as illustrated in FIG. 5B. In this state, the oxygen partial pressure at the outside electrode is smaller than that at the inside electrode as illustrated in FIG. 4C, so that a positive electromotive force is generated (see FIG. 5C) and negative current is then generated.

At the time of t=$t_0$, the air-fuel ratio controller switches the target air-fuel ratio from rich (A/F value is 14) to lean (A/F value is 15). The injection amount of fuel changes, and then the combustion property changes. The concentrations of hydrocarbon HC and carbon monoxide CO in the components of the exhaust gas are gradually decreased as time passes, whereas the concentration of oxygen $O_2$ is increased. The exhaust gas having the changed components is exhausted from the combustion chamber to reach the outside electrode 103 of the air-fuel ratio sensor. Now, a description will be given of the comparison between the high and low hydrogen atmospheres. In the high hydrogen atmosphere, hydrogen $H_2$ and oxygen $O_2$ are reacted in the vicinity of the outside electrode ($O_2+2H_2\rightarrow 2H_2O$), and then oxygen $O_2$ is consumed. The period from the time $t=t_0$ is set to the time V1 of the electromotive force is generated in the air-fuel ratio sensor is referred to as high concentration response period (T1), the air-fuel ratio controller switching the target air-fuel ratio from rich to lean at the time of $t=t_0$, V1 of the electromotive force indicating the lean air-fuel ratio (A/F value 15). As illustrated in FIG. 5C, the high oxygen concentration response period (T1) in the high hydrogen atmosphere is larger than the high oxygen concentration response period (T1') in the low hydrogen atmosphere. That is, T1>T1' is satisfied.

Figure 6A:
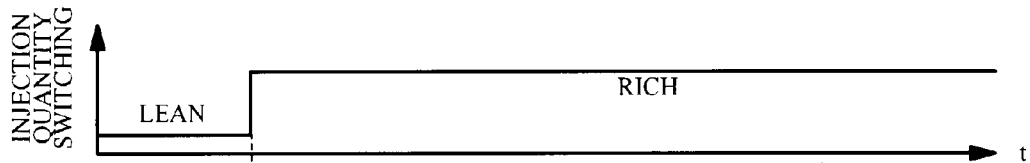
FIGS. 6A to 6C are views for describing time-series changes in the concentration of each component in the vicinity of the outside electrode of the air-fuel ratio sensor and time-series changes in the voltage of an $O_2$ sensor when the air-fuel ratio controller switches the target air-fuel ratio from lean to rich.
Figure 6B:
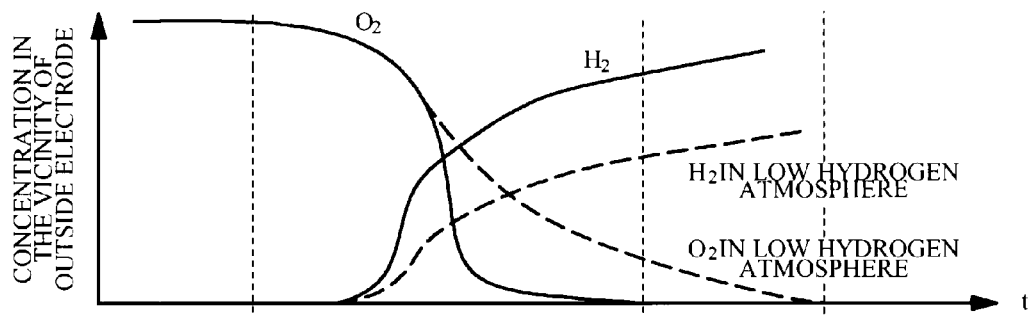
Figure 6C:
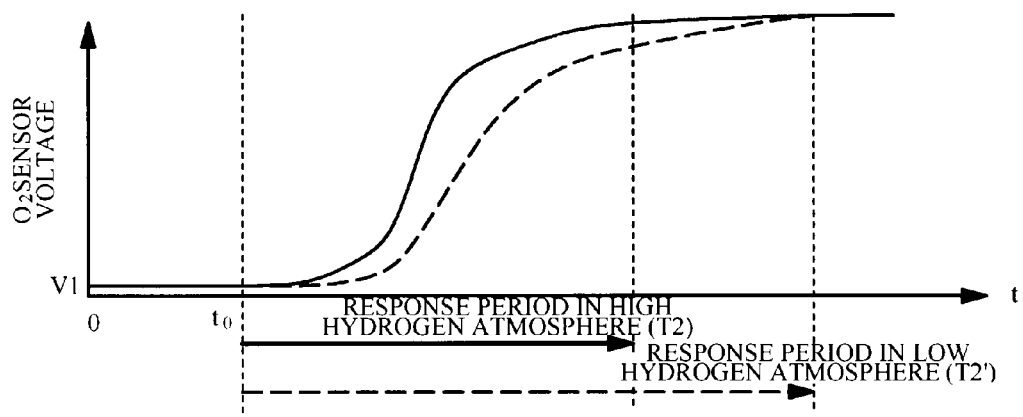

4. Response of the Air-Fuel Ratio Sensor to Switching of the Air Fuel Ratio from Lean to Rich A description will be given of how the response of the air-fuel ratio sensor changes, with reference to FIGS. 6A to 6C, when the air-fuel ratio controller switches the target air-fuel ratio from lean to rich, in a case where the exhaust gas is the high hydrogen atmosphere, and in a case where the exhaust gas is the low hydrogen atmosphere. FIG. 6B is a schematic view of concentration distribution of each component within the porous layer 104 in the vicinity of the outside electrode in time-series order. The high hydrogen atmosphere is indicated by solid lines, and the low hydrogen atmosphere is indicated by broken lines. FIG. 6C is a view of time-series changes in the voltage of the electromotive force generated between the both electrodes of the air-fuel ratio sensor. The high hydrogen atmosphere is indicated by solid lines, and the low hydrogen atmosphere is indicated by broken lines.

When the target air-fuel ratio is lean, a large amount of oxygen components of the exhaust gas are present in the vicinity of the outside electrode of the air-fuel ratio sensor. This state is indicated by $t<t_0$, as illustrated in FIG. 6B. In this state, the oxygen partial pressure at the outside electrode is larger than that at the inside electrode as illustrated in FIG. 4E, so that an electromotive force generated between the electrodes is 0 (see FIG. 6C) and positive current is then generated.

Figures 8A, 8B:
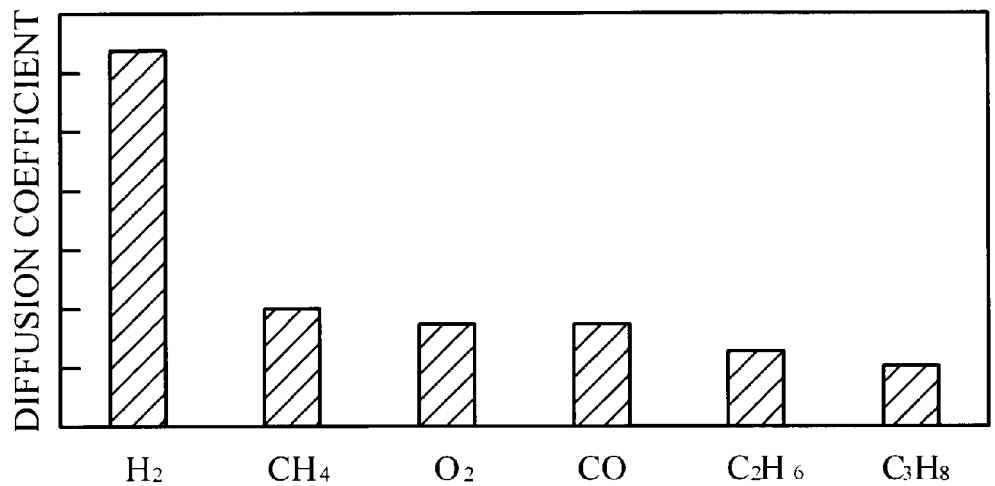
FIGS. 8A and 8B are a view and a table of diffusion coefficients, respectively.

At the time of $t=t_0$, the air-fuel ratio controller switches the target air-fuel ratio from the lean air-fuel ratio (A/F value is 15) to the rich air-fuel ratio (A/F value is 14). Then, the concentration of the oxygen is gradually decreased as time passed. In contrast, the concentrations of hydrocarbon HC and the carbon monoxide CO are increased. Referring now to FIGS. 8A and 8B, the diffusion speed of hydrogen $H_2$ is four times faster than that of oxygen $O_2$ or the like. Due to the difference in the diffusion speed, hydrogen $H_2$ reaches in the vicinity of the outside electrode earlier than the other components. Hydrogen $H_2$ and oxygen $O_2$ are reacted the vicinity of the outside electrode ($O_2+2H_2>2H_2O$), and then oxygen $O_2$ is consumed. In the high hydrogen atmosphere, oxygen $O_2$ is rapidly consumed. The period from the time $t=t_0$ is set to the time V2 of the electromotive force is generated in the air-fuel ratio sensor is referred to as low oxygen concentration response period (T2), the air-fuel ratio controller switching the target air-fuel ratio from lean to rich at the time of $t=t_0$, the V2 of the electromotive force indicating the rich air-fuel ratio (A/F value is 14). As illustrated in FIG. 6C, the high oxygen concentration response period (T2) in the high hydrogen atmosphere is smaller than the low oxygen concentration response period (T2') in the low hydrogen atmosphere. That is, T2<T2' is satisfied.

5. Principle of the Hydrogen Detecting Device which is Constructed by Combining the Air-Fuel Ratio Sensor and the Air-Fuel Ratio Controller As mentioned above, the high oxygen concentration response period (T1) is larger and the low oxygen concentration response period (T2) is smaller in the case of the high hydrogen atmosphere than the case of the low hydrogen atmosphere. By use of this, the detecting portion detects the information about the hydrogen concentration level. The detecting portion detects both of the high oxygen concentration response period (T1) and the low oxygen concentration response period (T2), and pays attention to the difference between the both (asymmetry property). That is, T(div) is calculated by the following arithmetic expression, and T(div) is interpreted as the hydrogen concentration level.

$$T(\text{div})=(\text{high oxygen concentration response period})/(\text{low oxygen concentration response period})=T1/T2$$

Additionally, in the present embodiment, the ratio is used to calculate T(div). However, in another aspect, the difference may be used to calculate the hydrogen concentration level.

$$T(\text{dif})=(\text{high oxygen concentration response period})-(\text{low oxygen concentration response period})=T1-T2$$

Figure 21:
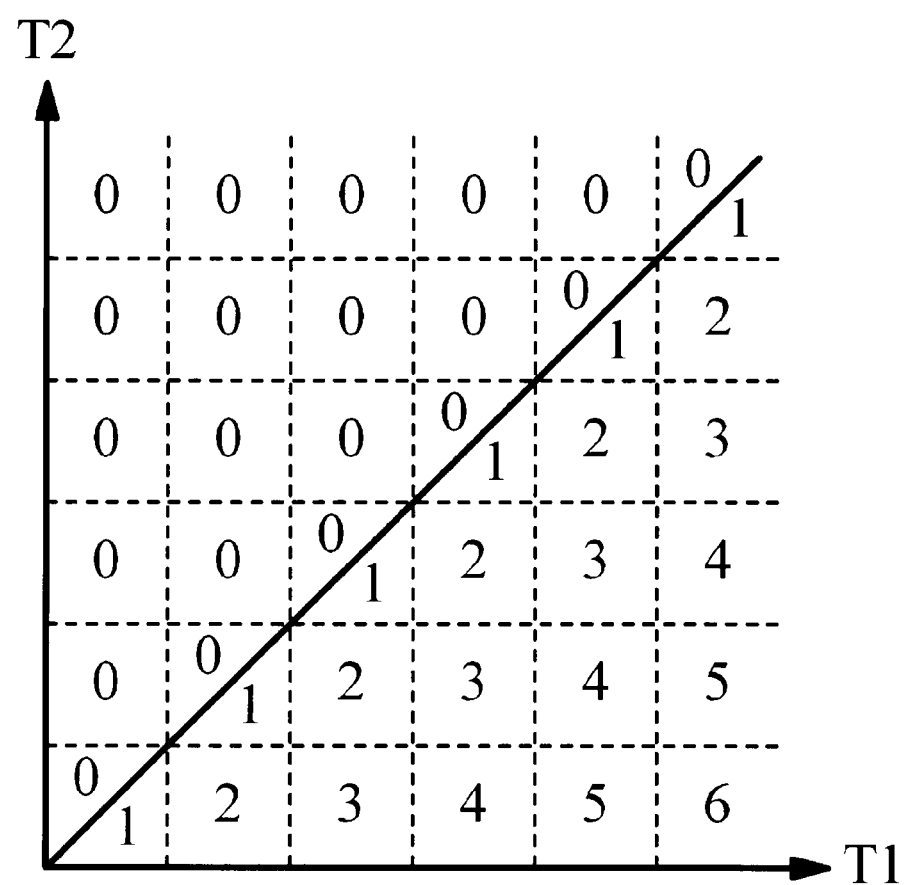
FIG. 21 is a map for obtaining T (Map) on the basis of T1 and T2.

In further another aspect, the experiment may be performed beforehand for associating the high and low oxygen concentration response periods with the hydrogen concentration level, a map illustrated in FIG. 21 may be recorded, and the hydrogen concentration level may be obtained by this map.

$$T(\text{Map})=\text{Map}((\text{high oxygen concentration response period}), (\text{low oxygen concentration response period}))$$

Figure 9:
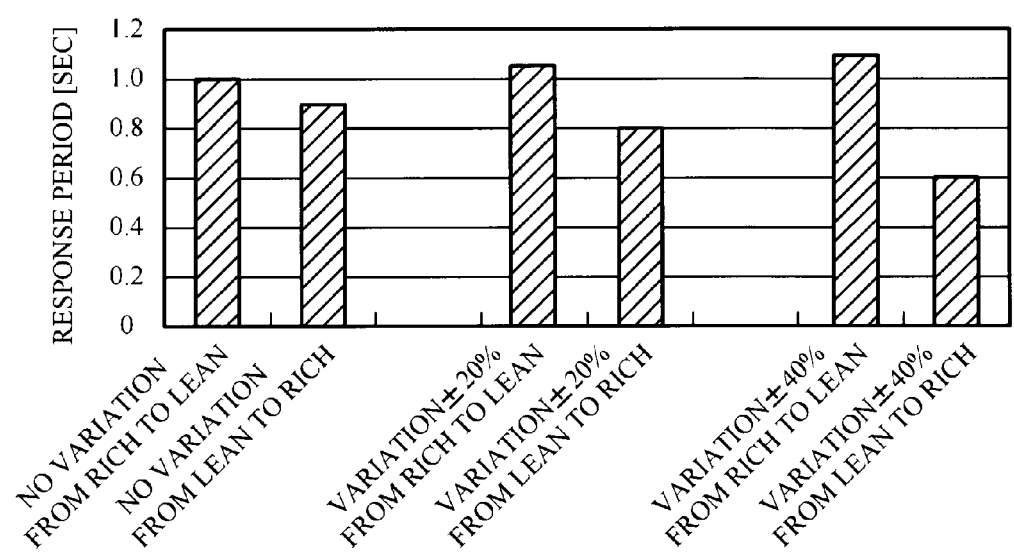
FIG. 9 is a view of response periods of the air-fuel ratio sensor in a case where a variation between the cylinders is caused and in a case where the variation between the cylinders is not caused.
Figure 10:
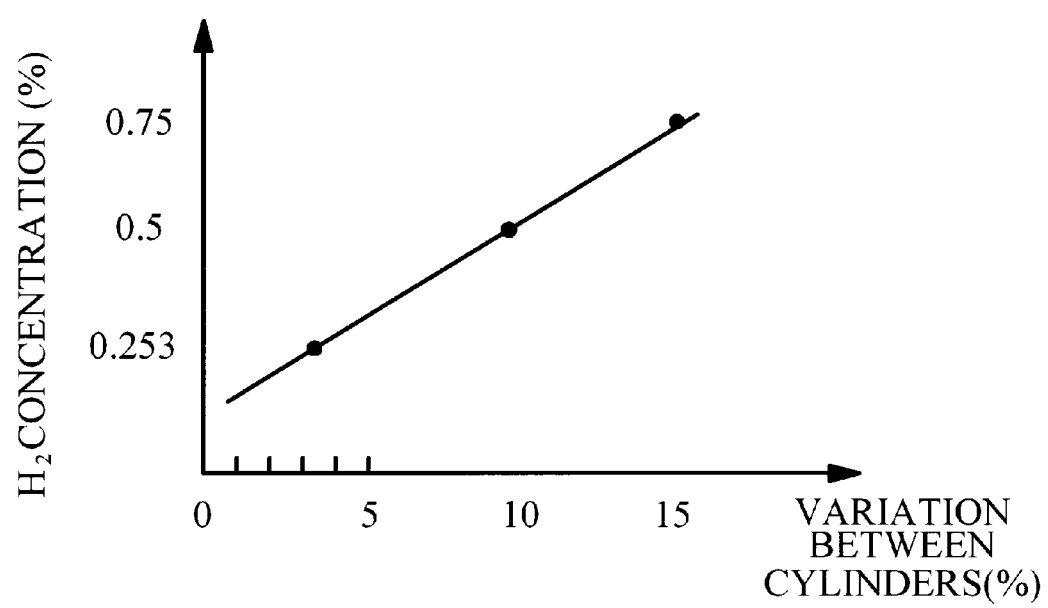
FIG. 10 is a view of a relationship between the degree (%) of the variation between the cylinders and the hydrogen concentration.
Figure 11:
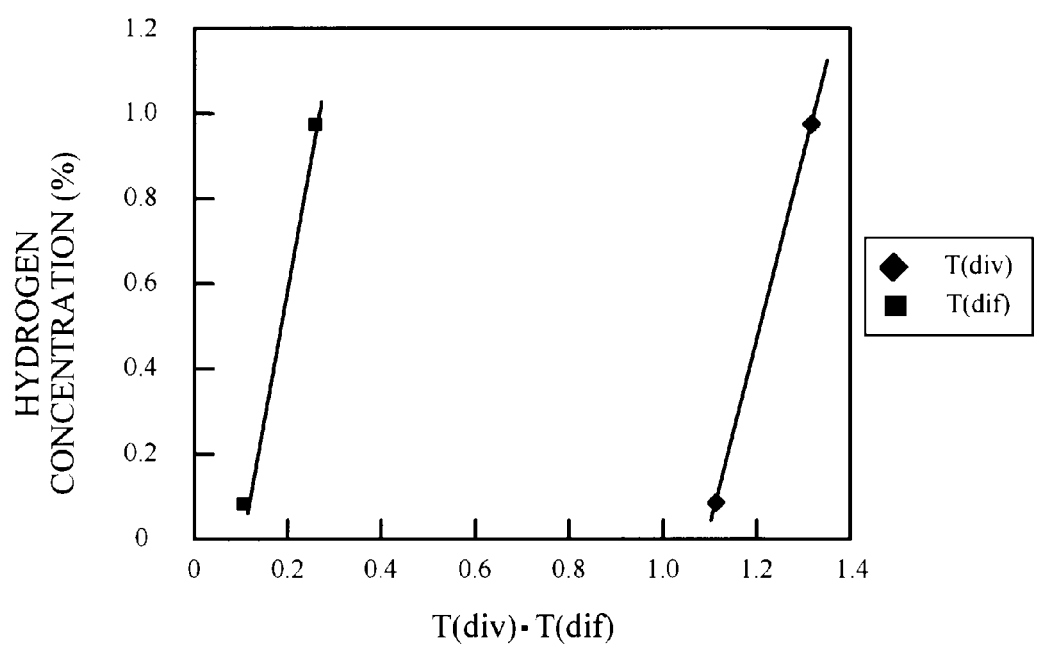
FIG. 11 is a view of relationships between T(div) and the hydrogen concentration and between T(dif) and the hydrogen concentration.
Figure 12A:
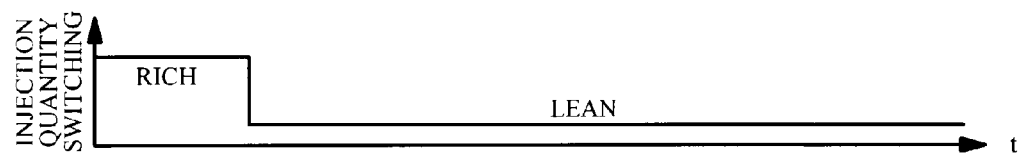
FIGS. 12A to 12C are views for describing time-series changes in the concentration of each component in the vicinity of the outside electrode of the air-fuel ratio sensor and time-series changes in the voltage of an $O_2$ sensor when the air-fuel ratio controller switches the target air-fuel ratio from rich to lean.
Figure 12B:
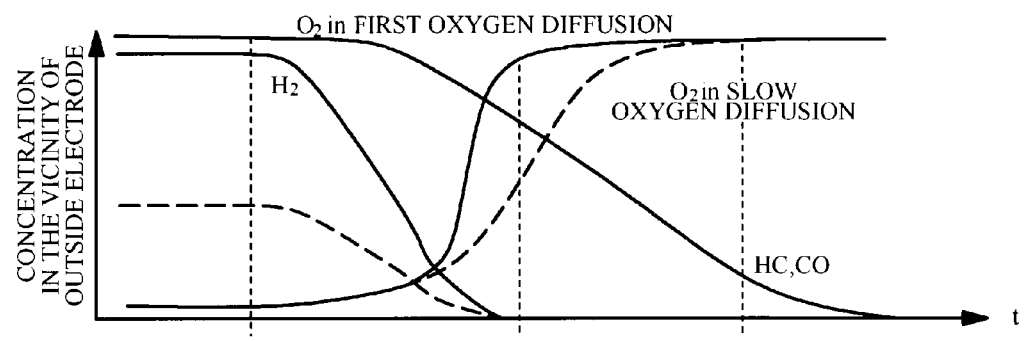
Figure 12C:
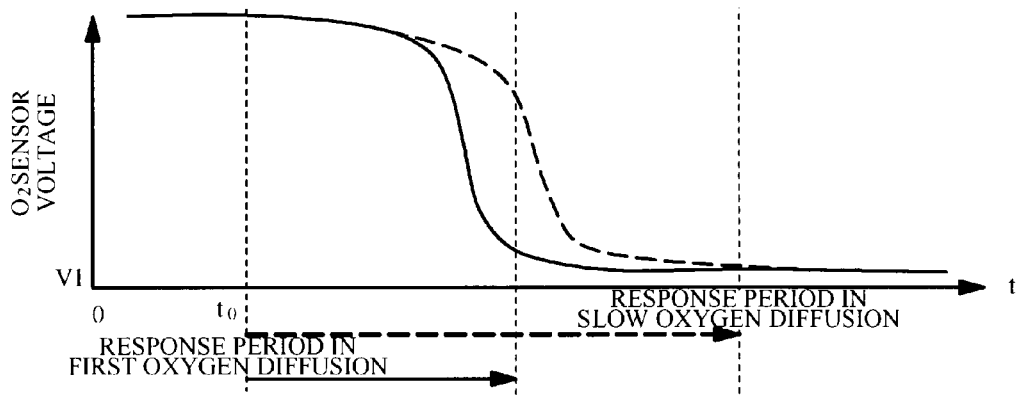
Figure 13A:
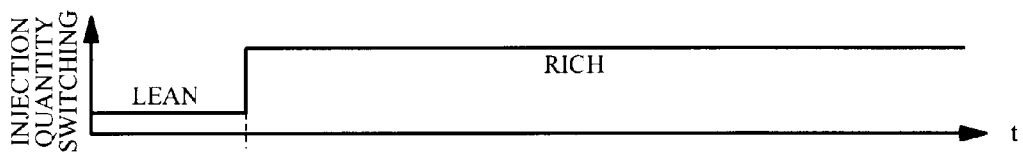
FIGS. 13A to 13C are views for describing time-series changes in the concentration of each component in the vicinity of the outside electrode of the air-fuel ratio sensor and time-series changes in the voltage of an $O_2$ sensor when the air-fuel ratio controller switches the target air-fuel ratio from lean to rich.
Figure 13B:
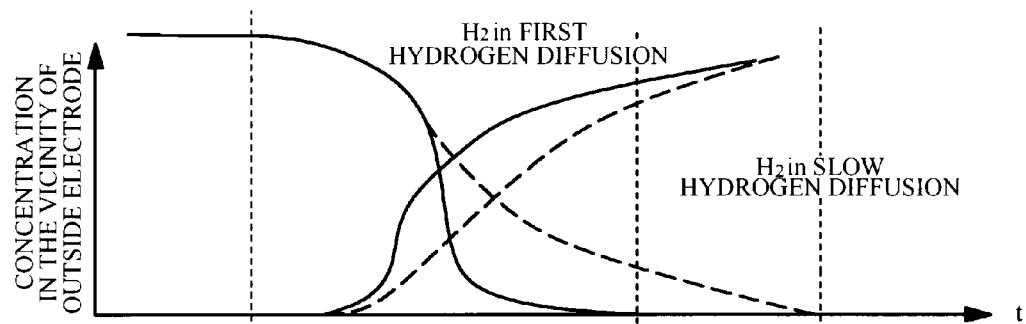
Figure 13C:
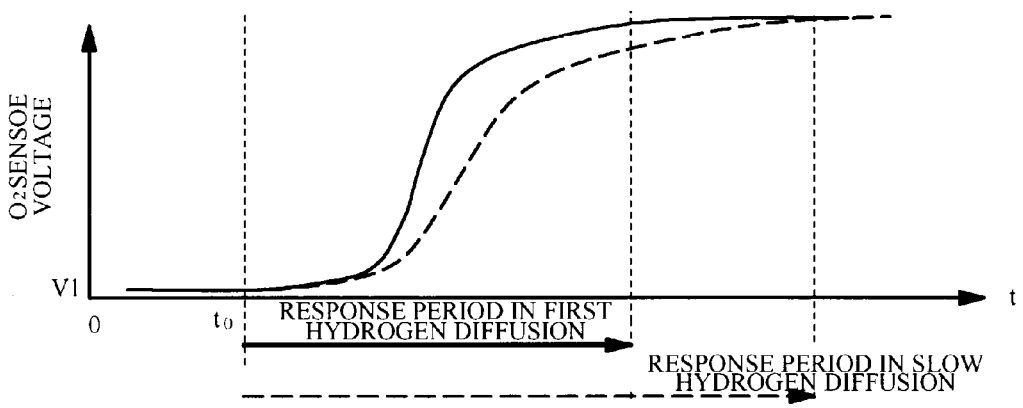

Numerical data of T(div) or T(dif) will be specifically represented. As will be described later, the dispersion between the cylinders and the hydrogen concentration (%) are correlated with each other, as illustrated in FIG. 10. The hydrogen concentration (%) illustrated in FIG. 10 is numerical data which are detected by another hydrogen sensor other than the hydrogen detecting device according to the present invention. FIG. 9 depicts the numerical data of the low and high oxygen concentration response periods in accordance with the degree of the dispersion between the cylinders. When the hydrogen concentrations of the cases where the dispersion between the cylinders are 0% and 20% are estimated based on FIGS. 9 and 10, the hydrogen concentrations are 0.08% and 0.98%, respectively. This relationships between the hydrogen concentration and T(div) and between the hydrogen concentration and T(dif) are illustrated in FIG. 11. In FIG. 11, the relationships between the hydrogen concentration and T(div) and between the hydrogen concentration and T(dif) are approximated to be linear, and are estimated to have a proportional relationship. However, the number of the samples may be increased by repeating the experiment, and the relationships between the hydrogen concentration level and T(div) and between the hydrogen concentration level and T(dif) may be approximated to be curved line.

The experiment may be performed beforehand, a map may be recorded, so that the relationships between the hydrogen concentration and T(div) and between the hydrogen concentration level and T(dif) may be defined. The relationships between the hydrogen concentration and T(div) and between the hydrogen concentration level and T(dif) are arbitrarily varied, depending on an initial state of the air-fuel ratio sensor employed.

The experiment for associating the high and low oxygen concentration response periods with the hydrogen concentration may be performed beforehand, a map may be recorded, and the hydrogen concentration may be obtained by an appropriate map.

hydrogen concentration (%)=Map2((high oxygen concentration response period), (low oxygen concentration response period))

In the following, a description will be given of the effect of a case where both of the high oxygen concentration response period (T1) and the low oxygen concentration response period (T2) are detected, attention is paid to the difference between the both (asymmetry property), T(div) as the ratio, T(dif) as the difference, or T(Map) as the map is calculated to be interpreted as the hydrogen concentration level, and the hydrogen concentration is detected.

As mentioned above, the high oxygen concentration response period is large in the high hydrogen atmosphere. For this reason, it is conceivable that the hydrogen concentration level or the hydrogen concentration is estimated by proportionating the hydrogen concentration level to the high oxygen concentration response period. Likewise, it is conceivable that the hydrogen concentration level or the hydrogen concentration is estimated by proportionating the hydrogen concentration level to the low oxygen concentration response period. However, if the hydrogen concentration is estimated by one of two response periods (high and low oxygen concentration response periods), there will be a problem. This is why these response periods are varied by the individual differences of the air-fuel ratio sensors, or by the diffusion speeds of hydrogen, oxygen, and the like.

The diffusion speed of oxygen molecule, hydrocarbon, or the like is varied by a difference in gas permeability (porosity) of the porous layer 104. Therefore, when the gas permeability is changed by the individual difference or by the deterioration with age, the difference in the diffusion speed in response thereto changes the sensor property. For example, when the porous layer 104 is slightly cracked (micro crack) due to the deterioration with age, the gas permeability is increased. Contrarily, when the porous layer 104 is clogged, the gas permeability is decreased. Thus, the sensor property is changed. Further, the diffusion speed is also changed, due to a combustion state of the internal combustion engine, a driving state, the temperature in atmosphere, the temperature in the internal combustion engine, and a change in the temperature caused by the circumstances inside and outside surroundings of the internal combustion engine. That is, the relationships between the high oxygen concentration response period and the hydrogen concentration and the relationship between the low oxygen concentration response period and the hydrogen concentration level are not unchangeable, and are changeable due to the surroundings, the deterioration with age, the individual difference in manufacture, and the like. For this reason, when the hydrogen concentration level is estimated on the basis of the high oxygen concentration response period, the error is increased. Likewise, when the hydrogen concentration level is estimated on the basis of the low oxygen concentration response period, there is a possibility that the error is increased.

However, when the hydrogen concentration level or the hydrogen concentration is detected on the basis of T(div) or T(dif), the hydrogen concentration detection error, which is caused by this problem, can be decreased. This will be described below.

A description will be given, with reference to FIGS. 12A to 12C and 13A to 13C, of a change in the response period, in a case where the gas permeability is changed by any cause and then the diffusion speed is changed. Likewise FIG. 5, in FIG. 12B, the concentrations of each component is represented by the vertical axis, and the output voltage of the air-fuel ratio sensor is illustrated in time series. Solid lines represent a case where the diffusion speeds of oxygen and hydrogen are large due to any cause. Broken lines represent a case where the diffusion speeds of oxygen and hydrogen are small. Referring to Figures, in the case where the diffusion speeds of oxygen and hydrogen are large, both of the high and low oxygen concentration response periods become small.

Accordingly, there is a relative small detection error, which is caused due to the difference in the gas permeability, of value of T(div) or T(dif) depending on the difference between T1 and T2 (asymmetry property). In the method, according to the present embodiment, for estimating the hydrogen concentration level or the hydrogen concentration by use of T(div) or T(dif), the detection error is made smaller than that of the method for associating the high oxygen concentration response period with the hydrogen concentration level or the hydrogen concentration or than that of the method for associating the low oxygen concentration response period with the hydrogen concentration level or the hydrogen concentration. In other words, in the present embodiment, it is made possible to detect the hydrogen concentration level and the hydrogen concentration with a smaller detection error caused by the circumstances, the deterioration with age, or the individual difference in manufacture.

6. Flowchart of Detecting Hydrogen Concentration Level

Figure 14:
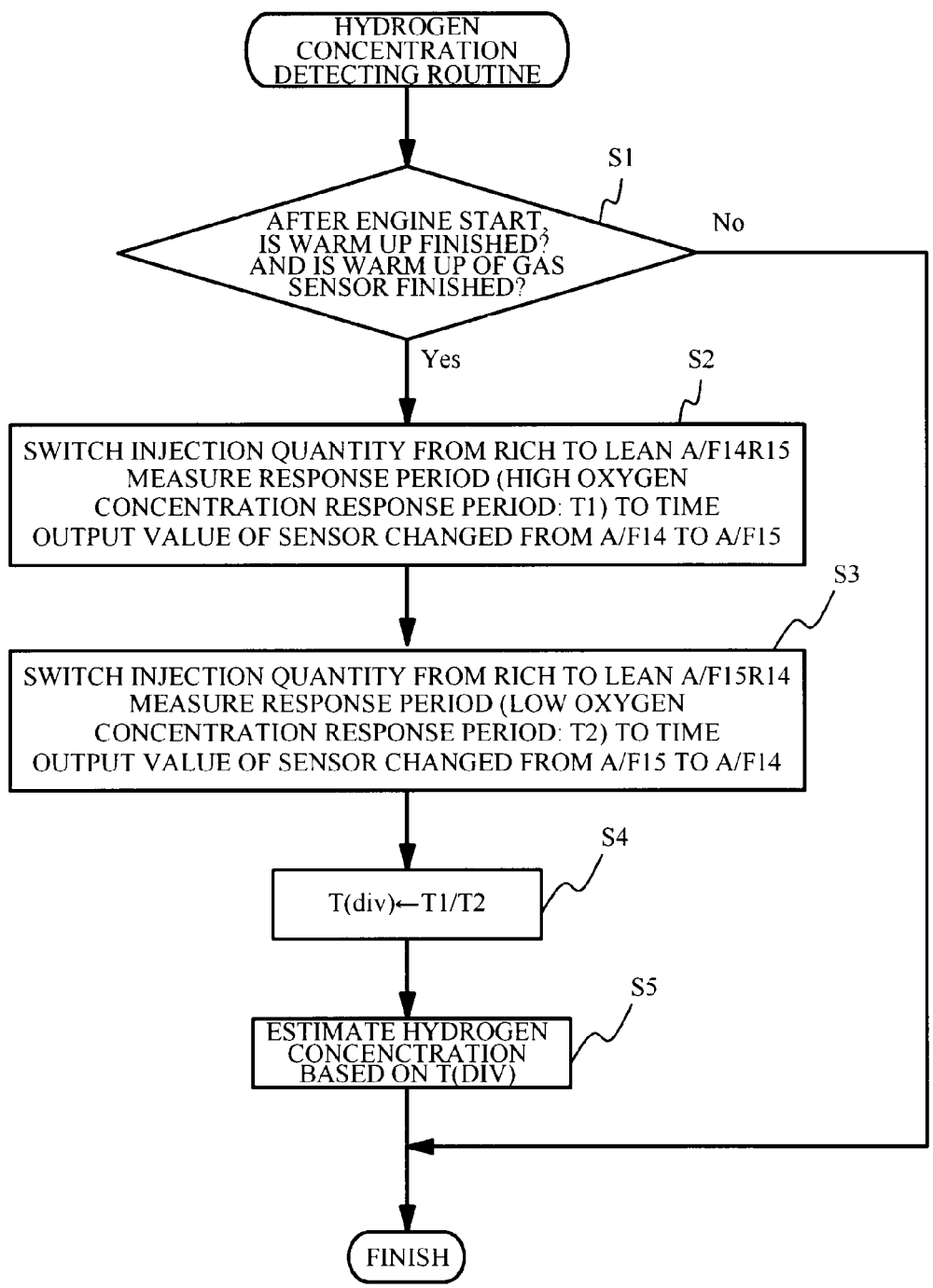
FIG. 14 is a view of a hydrogen concentration detection routine according to a first embodiment.

There has been described heretofore the operation principle and the effect according to the method for detecting the hydrogen concentration level and the hydrogen concentration by the air-fuel ratio sensor. In the following, a description will sequentially be given, with reference to a flowchart illustrated in FIG. 14, of the detection of the hydrogen concentration level and the hydrogen concentration by use of the hydrogen detecting device according to the present embodiment. Such a hydrogen concentration detection routine is performed by the ECU 1.

First, it is decided whether the following all conditions are met in S1. When all the conditions are met, the processing goes to S2. When any one of all the conditions is not met, this routine is finished.

(1) Warm-up of the engine is finished. (for example, the coolant temperature is higher than or equal to a given value)

(2) Warm-up of the air-fuel ratio sensor is finished.

In this step, it is decided that the warm-up of the internal combustion engine is finished and the temperature of the air-fuel ratio sensor reaches the activation temperature to detect the components of the exhaust gas. This prevents the calculation error of the hydrogen concentration level or the hydrogen concentration. In addition, the following condition may be added.

(3) It is not decided that the air-fuel ratio sensor is abnormal (failure).

Next, the high concentration response period T1 is measured in S2. The air-fuel ratio controller switches the target air-fuel ratio from rich to lean, that is, switches the A/F value from 14 to 15, and this time is set to $t=t_0$. The period from this timing to the time the output value of the air-fuel ratio sensor is switched from the A/F value 14 to the A/F value 15 and the voltage V1 corresponding to the A/F value 15 is detected, is measured to be the response period. This response period is referred as to the high oxygen concentration response period (T1).

Next, the low concentration response period T2 is measured in S3. The air-fuel ratio controller switches the target air-fuel ratio from lean to rich, that is, switches the A/F value from 15 to 14, and this time is set to t=t₀. The period from this timing to the time the output value of the air-fuel ratio sensor is switched from the A/F value 15 to the A/F value 14 and the voltage V2 corresponding to the A/F value 14 is detected, is measured to be the response period. This response period is referred as to the low oxygen concentration response period (T2).

Next, the difference between T1 and T2 is calculated in S3. That is, $$T(div) = (high\ oxygen\ concentration\ response\ period / low\ oxygen\ concentration\ response\ period) = T1/T2$$

is calculated. T(div) is interpreted to the hydrogen concentration. Next, in S4, the map illustrated in FIG. 11 is read to calculate the hydrogen concentration (%) from T(div).

The detection portion performs the measurement in S2 and S3 in the flowchart and the calculation of T(div) in S4. The ECU 1 includes the air-fuel ratio controller and the detecting portion. The ECU 1 and the upstream side air-fuel ratio sensor 10 or the ECU 1 and the downstream side air-fuel ratio sensor 11 correspond to the hydrogen detecting device.

In the flowchart according to the present embodiment, A/F value 14 is employed as a lean target air-fuel ratio set by the air-fuel ratio controller, and A/F value 15 is employed as a rich target air-fuel ratio. This means that the air-fuel ratio controller temporarily stops the air-fuel ratio feedback control in the internal combustion engine where the air-fuel ratio feedback control is being performed, and the target air-fuel ratio is controlled in order to detect the hydrogen concentration level or the hydrogen concentration. In this manner, A/F values 14 and 15 are employed and the air-fuel ratio controller temporarily stops the air-fuel ratio feedback control, so that the response period is relatively large values about 0.5 seconds to about 1.1 seconds as illustrated in FIG. 9. For this reason, the difference in the response period (asymmetry property), which is caused due to the difference in the diffusion speed of hydrogen and oxygen, becomes large, thereby allowing precise detection of the hydrogen concentration level and the hydrogen concentration.

7. Another Aspect of the Present Embodiment

In the present embodiment, A/F value 14 is employed as the lean target air-fuel ratio set by the air-fuel ratio controller, and A/F value 15 is employed as the rich target air-fuel ratio. However, another A/F value may be employed according to another aspect. The air-fuel ratio controller has only to switch the target air-fuel ratio across the theoretical air-fuel ratio to set a predetermined target air-fuel ratio. The A/F values of the lean air-fuel ratio and the rich air-fuel ratio may be set to any approximate value of the theoretical air-fuel ratio, in order to perform this routine while the air-fuel ratio feedback control is being performed.

Additionally, in the present embodiment, the high oxygen concentration response period T1 is defined as a period from the time t=t₀ is set to the time V1 of the electromotive force corresponding to the A/F value 15 is generated in the air-fuel ratio sensor. The low oxygen concentration response period T2 is defined as a period from the time t=t₀ is set to the time V2 of the electromotive force corresponding to the A/F value 14 is generated in the air-fuel ratio sensor. However, according to another aspect of the present embodiment, V1 and V2 may be arbitrarily changed. V1' may be defined as any value between V0 (0.5 V) to V1, which is an approximate value of V1, and T1 may be defined as the period from the time t=t₀ is set to the time V1' of the electromotive force is generated in the air-fuel ratio sensor. V2' may be defined as any value from V0 (0.5 V) to the V2, which is an approximate value of the V2, and T2 may be defined as the period from the time t=t₀ is set to the time the V2' of the electromotive force is generated in the air-fuel ratio sensor.

In another aspect of the present embodiment, the start times of the measurement of T1 and T2 may be arbitrarily changed. T1 may be defined as the period from a given point of time that passes t₀, for example, after the air-fuel ratio sensor detects the voltage (0.5 V) corresponding to the theoretical air-fuel ratio, to the time voltage of V1 is detected. T2 may be defined as the period from the time a given point of time that passes t₀, for example, after the air-fuel ratio sensor detects the voltage V0 (0.5 V) corresponding to the theoretical air-fuel ratio, to the time voltage of V2 is detected.

8. Effects of the present embodiment

The hydrogen concentration level or the hydrogen concentration is detected by using this hydrogen detecting device with the air-fuel ratio sensor and the air-fuel ratio controller, so as to enable characteristic control, whereby the information about the hydrogen concentration level or the hydrogen concentration is detected at low cost. Further, the hydrogen concentration level or the hydrogen concentration is detected by paying attention to the difference (asymmetry property) between the high and low oxygen concentration response periods, whereby the information about the hydrogen concentration level or the hydrogen concentration is detected with the detection error reduced.

[Second Embodiment]

A description will be given, in the following order, of an internal combustion engine abnormality deciding device, which decides whether or not the problem of a variation between the cylinders is caused, and to which the hydrogen detecting device according to the present invention is applied.

1. Regarding the variation between the cylinders and the generation of hydrogen
2. A deciding method by use of the hydrogen detecting device (flowchart)

1. Regarding the Variation Between the Cylinders and the Generation of Hydrogen

It is preferable that the abnormality of the internal combustion engine should be early detected in light of the improvement of the exhaust emission. The abnormal combustion is one of the internal combustion engine abnormalities. One factor thereof is that fuel injection quantity or intake air quantity in a given cylinder is increased or decreased due to any cause in the internal combustion engine having plural cylinders. The problem that the combustion is varied between the cylinders is referred to as a problem of the variation between the cylinders. The variation between the air-fuel ratio and the target air-fuel ratio in each cylinder is referred to as the variation between the cylinders (%).

If the problem of the variation between the cylinders is caused, there will be a problem that the fuel consumption and the exhaust emission are degraded. Japanese Unexamined Patent Publication No. 2006-152845 discloses a technique for estimating the air-fuel ratio of each cylinder. However, in this method, in order to precisely measure the air-fuel ratio of each cylinder, the air-fuel ratio sensor has to be arranged at the gathering portion of the exhaust pipe. This causes problems that the attachment position of the sensor against the exhaust pipe is limited and the design freedom of the exhaust pipe is limited.

As illustrated in FIG. 7, when the target air-fuel ratio is the rich air-fuel ratio, hydrogen is generated by the combustion of the engine. This will be described. Since a large amount of the fuel is injected as compared to a case of the theoretical air-fuel ratio, water $H_2O$, carbon monoxide CO, unburned hydrocarbon HC, and the like are generated in the combustion chamber. The combustion chamber and the exhaust manifold have high temperatures to promote the redox reaction. The components of the exhaust gas in the exhaust pipe are reacted.

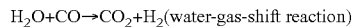
$H_2O + CO \rightarrow CO_2 + H_2$ (water-gas-shift reaction)

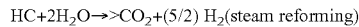
$HC + 2H_2O \rightarrow CO_2 + (5/2) H_2$ (steam reforming)

In this manner, the water gas reduction reaction is carried out. Thus, hydrogen is generated. The higher the temperature is, or the richer the air-fuel ratio of the exhaust gas is, that is, the larger the amount of unburned hydrocarbon HC and carbon monoxide CO are, the more frequently this reaction is carried out. Accordingly, the richer and the higher the gas is, the larger hydrogen concentration in the exhaust gas is. Thus, when the air-fuel ratio is rich, the main components are hydrogen $H_2$, methane $CH_4$, carbon monoxide CO, carbon dioxide $CO_2$, and the like.

Here, when the variation between the cylinders is caused, the air-fuel ratio of the exhaust gas involuntarily becomes richer than the target air-fuel ratio in a given cylinder. Then, a large amount of hydrogen is generated. The exhaust gas exhausted from this cylinder and the exhaust gas exhausted from another cylinder are gathered in the gathering portion 37, hydrogen will flow into the downstream of the gathering portion 37. This is because the gas component reacting with hydrogen and canceling it is not generated in another cylinder. In this way, when the variation between the cylinders is caused, the concentration of hydrogen is higher in the exhaust pipe (see FIG. 10). Moreover, when the variation between the cylinders is caused, the air-fuel ratio of the exhaust gas in a give cylinder is richer than the target air-fuel ratio, whereas the air-fuel ratio of the exhaust gas in another cylinder is lean. Then, the rich exhaust gas and the lean exhaust gas are combined in the downstream side of the gathering portion 37, so that the target air-fuel ratio may be detected in light of the oxygen concentration. For this reason, in the deciding method for detecting the air-fuel ratio (oxygen concentration) by use of the air-fuel ratio sensor arranged on the downstream side of the gathering portion 37, it is impossible to detect that there is a variation between the cylinders. Therefore, in the present embodiment, hydrogen in the exhaust pipe is detected by the technique according to the first embodiment and by use of the upstream side air-fuel ratio sensor 10 and the air-fuel ratio controller.

2. A deciding method by use of the hydrogen detecting device (flowchart)

Figure 15:
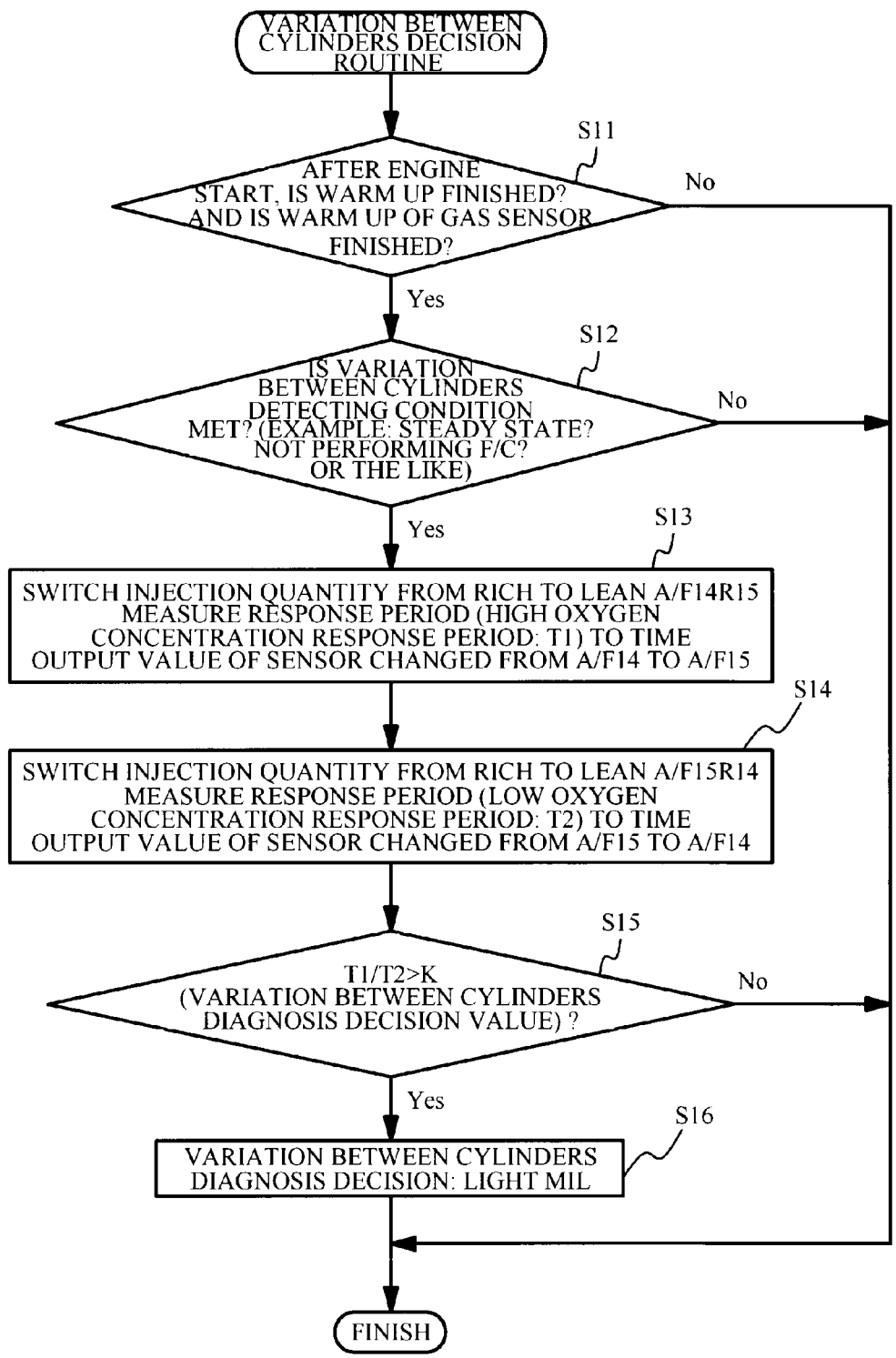
FIG. 15 is a view of the variation between the cylinders decision routine according to a second embodiment.

The internal combustion engine abnormality deciding device according to the present embodiment detects hydrogen contained in the exhaust gas by use of the upstream side air-fuel ratio sensor 10. In the following, a description will sequentially be given, with reference to a flowchart illustrated in FIG. 15, of the decision of the variation between the cylinders by the internal combustion engine abnormality deciding device according to the present embodiment. This deciding routine of the variation between the cylinders is performed by the ECU 1. The ECU 1 performs this routine every ten minutes, for example.

First, it is decided whether or not the following conditions are met in S11.

When all the conditions are met, the processing goes to S12. When at least one of all the conditions is not met, this routine is finished.

(1) Warm-up of the engine is finished.
(2) Warm-up of the air-fuel ratio sensor is finished.

In this step, it is decided that the warm-up of the internal combustion engine is finished and the temperature of the air-fuel ratio sensor reaches the activation temperature to detect the components of the exhaust gas. This prevents the calculated error of the hydrogen concentration level or the hydrogen concentration. Further, the following condition may be added.

(3) It is not decided that the air-fuel ratio sensor is abnormality (failure).

In S12, it is decided whether or not the condition for detecting the variation between the cylinders is met. This decides whether the steady drive state is performed and whether the fuel cut is not performed. When these two conditions are met, the processing goes to S13. When at least one of the two conditions is not met, this routine is finished. When the condition that the variation between the cylinders cannot be detected is beforehand recognized in this step, the decision of the variation between the cylinders is not performed.

Figure 16:
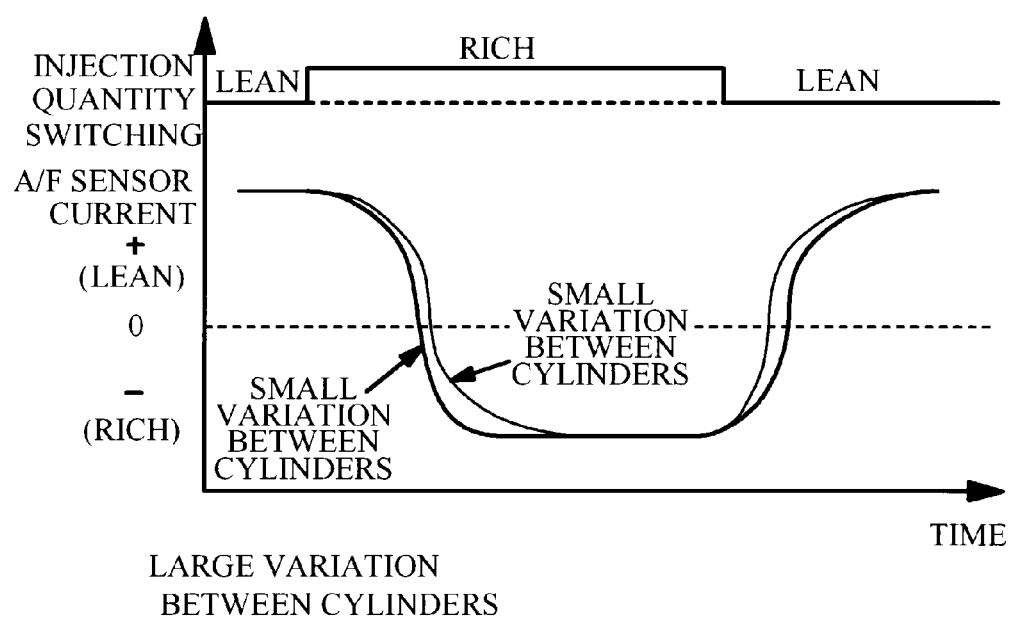
FIG. 16 is a view for describing that the response of current detected by the A/F sensor changes between a case where the variation between the cylinders is great and a case where the variation between the cylinders is small.
Figure 17:
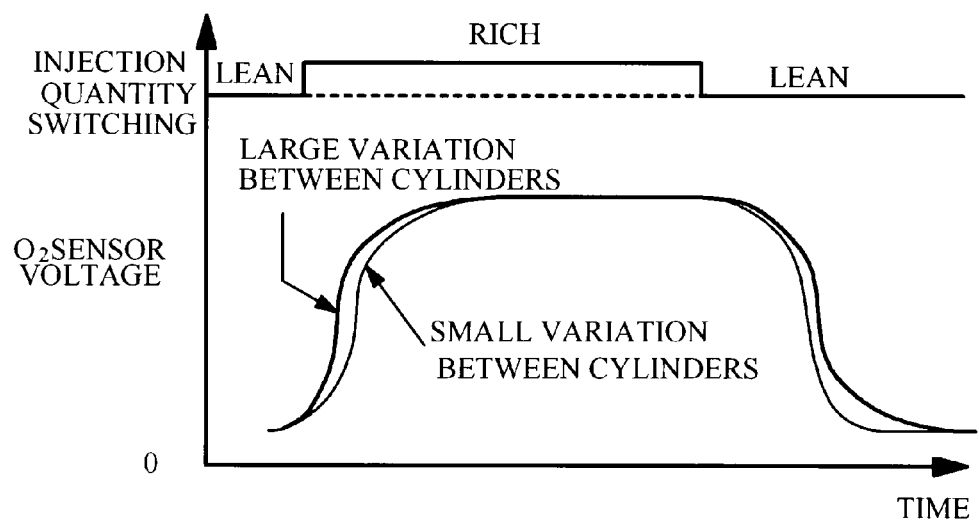
FIG. 17 is a view for describing a change in response of voltage detected by the $O_2$ sensor in a case where the variation between the cylinders is great and in a case where the variation between the cylinders is small.

S13 and S14 are respectively similar to S2 and S3, so that their descriptions will be omitted. As illustrated in FIGS. 16 and 17, the air-fuel ratio controller switches the target air-fuel ratio from lean to rich, or from rich to lean. As illustrated in these figures, it is preferable that the air-fuel ratio controller should continuously switch and the detecting portion should continuously measure T1 and T2.

In S15, it is decided whether or not T1/T2>K is met. When this condition is established, the processing goes to S16, so it is decided that the variation between the cylinders is caused, and then the MIL lamp 22 is turned on. When this condition is not met, this routine is finished. This K is a value set beforehand as a diagnosis decision value. The T1/T2 corresponds to T(div) in the first embodiment, and to the hydrogen concentration level. That is, it is decided whether or not the hydrogen concentration level is greater than or equal to a given value in S15. In this step, it is decided the variation between the cylinders is caused, when the hydrogen concentration level is greater than or equal to the given value.

The detecting portion performs the measurements in S13 and S14 of the flowchart and the calculation of T1/T2 in S15. The decision in S15 is performed by the abnormality deciding portion. The ECU 1 includes the air-fuel ratio controller, the detecting portion, and the abnormality deciding portion. The ECU 1 and the upstream side air-fuel ratio sensor 10 correspond to the internal combustion engine abnormality deciding device.

The variation between the cylinders diagnosis decision value K may be defined by a map defining the relationship between the number of engine revolutions and the engine load. The air-fuel ratio sensor may be arranged at any position where it can detect the exhaust gas. In this way, the arrangement position of the air-fuel ratio sensor is not limited, and the design of the exhaust pipe is not limited, either. Thus, the exhaust pipe can be freely designed. Preferably, the air-fuel ratio sensor is arranged at the upstream of the exhaust purifying catalyst and the downstream of the gathering portion 37. In other words, it is preferable that the upstream side air-fuel ratio sensor 10 should be used. Further preferably, the air-fuel ratio sensor is arranged in the upstream of the exhaust purifying catalyst, in the vicinity of the exhaust purifying catalyst, and in such a position to avoid getting wet with the condensate water. This is because once the air-fuel sensor gets wet with the condensate water, the air-fuel ratio sensor may be abnormal.

The decision of the variation between the cylinders is performed in this way so that the information about the hydrogen concentration level is detected by the technique of the first embodiment. It is therefore possible to detect the variation between the cylinders with a few detection error, which is caused by the temperature, the individual difference of the air-fuel ratio sensor, and the like, at low cost. Further, the arrangement position of the air-fuel ratio sensor is not limited, and the exhaust pipe can be freely designed. Furthermore, the air-fuel ratio sensor is arranged in the downstream of the gathering portion, thereby avoiding getting wet with the condensate water and avoiding the abnormality of the air-fuel ratio sensor.

[Third Embodiment]

A description will be given, in the following order, of the internal combustion engine abnormality deciding device, which decides whether or not the exhaust purifying catalyst is degraded, and to which the hydrogen detecting device according to the present invention is applied.

1. Catalyst degradation and water-gas-shift reaction
2. A deciding method by use of the hydrogen detecting device (flowchart)

1. Catalyst Degradation and Water-Gas-Shift Reaction

The exhaust purifying catalyst degradation is the abnormality of the exhaust gas purifying system of the internal combustion engine as one of the internal combustion engine abnormalities. Hereinafter, it is referred to as the problem of the catalyst degradation. The exhaust purifying catalyst adsorbs unburned hydrocarbon HC, nitric oxide $NO_x$, carbon monoxide CO, and reduces and releases these components. When the exhaust purifying catalyst is degraded not to normally purify the exhaust gas, the unpurified exhaust gas may be released into the atmosphere, and the exhaust emission is degraded.

There is known a technique for estimating the oxygen storage capacity (OSC) as a method for deciding whether the exhaust purifying catalyst is degraded. The recent research develops the exhaust purifying catalyst slightly using a noble metal. Hence, the correlative relationship between the oxygen storage capacity and the degradation of the exhaust purifying catalyst is weakened. Therefore, it is necessary to establish another method for deciding the degradation of the exhaust purifying catalyst without detecting the oxygen storage capacity. Once the exhaust purifying catalyst is degraded, the noble metal within the exhaust purifying catalyst is removed to lower the activation level, so that the reducing ability is lowered. Then, the reactivity of the water-gas-shift reaction ($H_2O+CO \rightarrow CO_2+H_2$) is lowered, so that the amount of hydrogen generated in the downstream of the exhaust purifying catalyst is made small. That is, the new exhaust purifying catalyst generates a large amount of hydrogen, whereas the degraded exhaust purifying catalyst generates a small amount of hydrogen. By detecting the hydrogen in the downstream of the exhaust purifying catalyst, the degradation of the exhaust purifying catalyst slightly using the noble metal is decided with accuracy, as compared to the decision depending on the oxygen storage capacity. Japanese Unexamined Patent Publication No. 2003-120383 discloses a technique for arranging a hydrogen sensor and an exhaust gas air-fuel ratio sensor in the downstream of the catalyst. However, the provision of the hydrogen sensor for the abnormality decision causes a problem of cost. Therefore, in the present embodiment, hydrogen in the downstream of the exhaust purifying catalyst is detected by the technique according to the first embodiment and by use of the downstream side air-fuel ratio sensor 11 and the air-fuel ratio controller.

2. a Deciding Method by Use of the Hydrogen Detecting Device (Flowchart)

Figure 18:
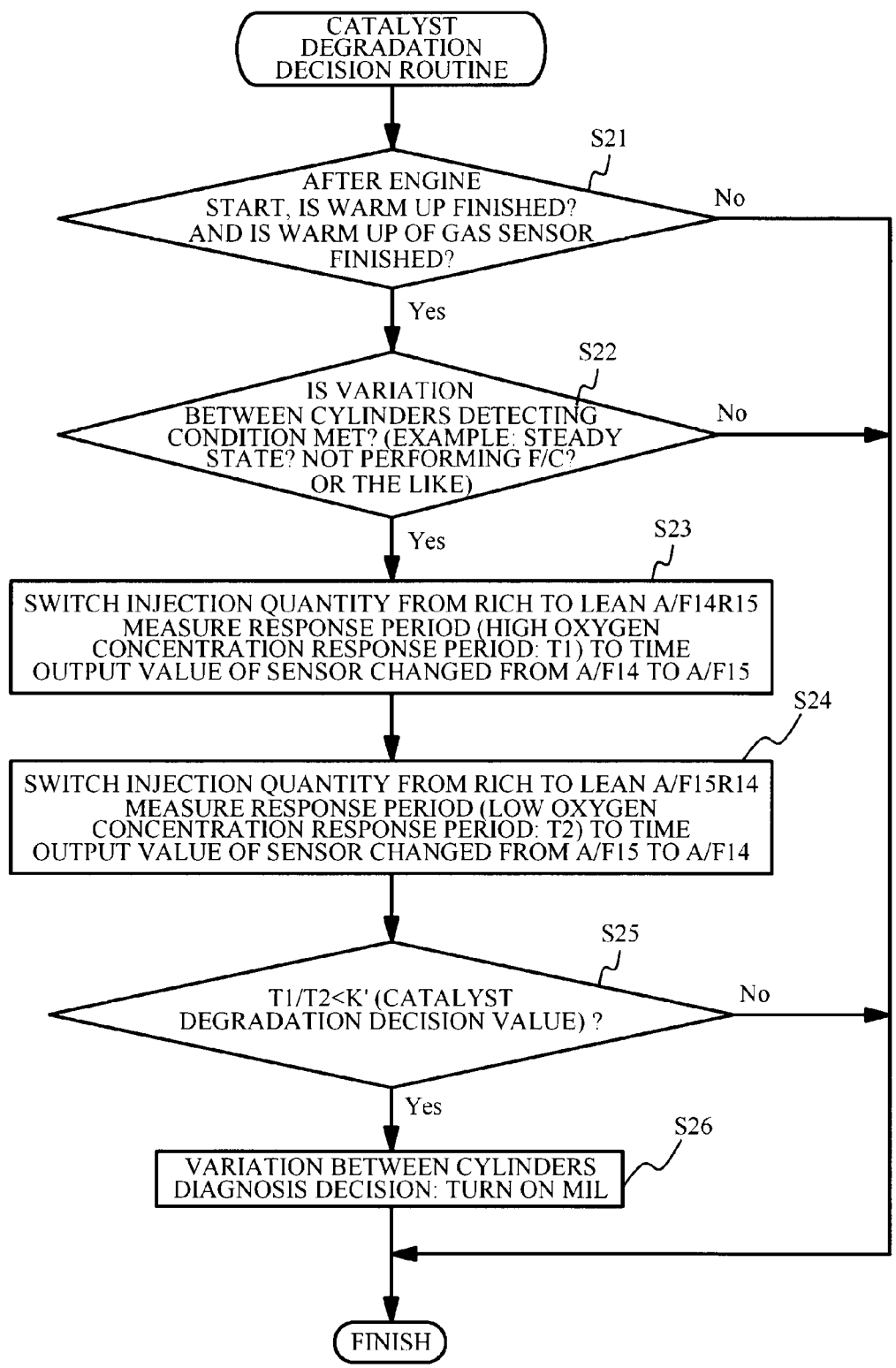
FIG. 18 is a view of an exhaust purifying catalyst degradation decision routine according to a third embodiment.

The internal combustion engine abnormality deciding device according to the present embodiment detects the hydrogen contained in the exhaust gas by use of the downstream side air-fuel ratio sensor 11. In the following, a description will be given, with reference to FIG. 18, of the exhaust purifying catalyst degradation decision by use of the internal combustion engine abnormality deciding device according to the present embodiment. This catalyst degradation decision routine is performed by the ECU 1. The ECU 1 performs this routine, for example, every ten minutes.

First, it is decided whether or not all the following conditions are met in S21. When all the conditions are met, the processing goes to S22. When at least one of the conditions is not met, this routine is finished.

(1) Warm-up of the engine is finished.
(2) Warm-up of the air-fuel ratio sensor is finished.
(3) Warm-up of the exhaust purifying catalyst is finished.

In this step, it is decided that the warm-up of the internal combustion engine is finished and the temperature of the air-fuel ratio sensor reaches the activation temperature to detect the components of the exhaust gas. This prevents the error decision. Further, the following condition may be added.

(4) It is not decided that the air-fuel ratio sensor is abnormal (failure).

It is decided whether or not the condition for detecting the catalysis degradation is met in S22. This decides whether the steady drive state is performed and whether the fuel cut is not performed. When these two conditions are met, the processing goes to S23. When any one of two conditions is not met, this routine is finished. When the condition that the degradation of the exhaust purifying catalyst cannot be detected is recognized beforehand in this step, the degradation decision of the exhaust purifying catalyst is not performed.

Figure 19:
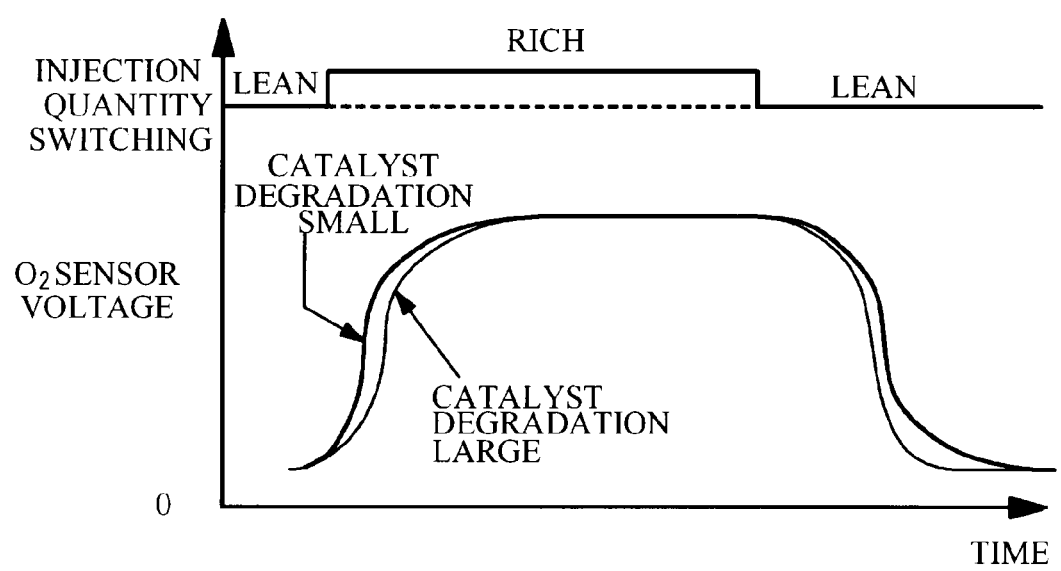
FIG. 19 is a view for describing that the response of current detected by the A/F sensor changes between a case where the exhaust purifying catalyst degradation is great and a case where the exhaust purifying catalyst degradation is small.
Figure 20:
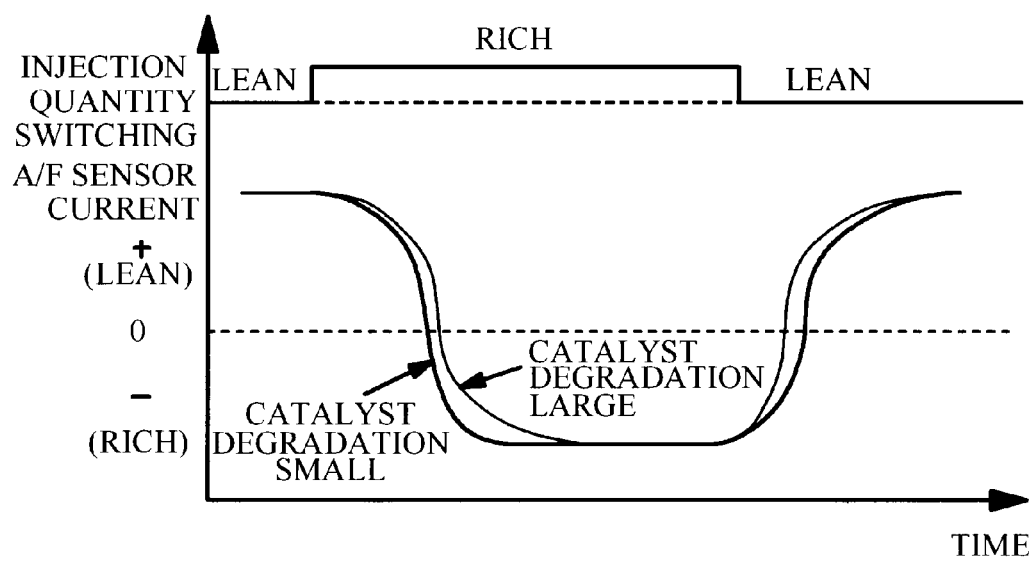
FIG. 20 is a view for describing the response of voltage detected by the $O_2$ sensor changes between a case where the exhaust purifying catalyst degradation is great and a case where the exhaust purifying catalyst degradation is small.

S23 and S24 are respectively similar to S13 and S14, so that their descriptions will be omitted. As illustrated in FIGS. 19 and 20, the air-fuel ratio controller switches the target air-fuel ratio from lean to rich, or from rich to lean. As illustrated in these figures, it is preferable that the air-fuel ratio controller continuously switches the target air-fuel ratio and the detecting portion continuously measures the above T1 and T2.

In S25, it is decided whether or not T1/T2<K' is met. When this condition is met, the processing goes to S26, so it is decided that the degradation of the exhaust purifying catalyst is caused, and then the MIL lamp 22 is turned on. When this condition is not met, this routine is finished. This K is a value which is set beforehand as a catalytic degradation decision value. T1/T2 corresponds to T(div) in the first embodiment, and to the hydrogen concentration level. That is, it is decided whether or not the hydrogen concentration level is smaller than or equal to a given value in S25. In this step, it is decided the degradation of the exhaust purifying catalyst is caused, when the hydrogen concentration level is smaller than or equal to the given value.

The detecting portion performs the measurements in S23 and S24 of the flowchart and the calculation of T1/T2 in S25. The decision in S25 is performed by the abnormality deciding portion. The ECU 1 includes the air-fuel ratio controller, the detecting portion, and the abnormality deciding portion. The ECU 1 and the downstream side air-fuel ratio sensor 11 correspond to the internal combustion engine abnormality deciding device.

The catalytic degradation decision value K' may be defined by a map defining the relationship between the number of engine revolutions and the engine load. The air-fuel ratio sensor may be arranged at any position where the exhaust gas can be detected.

Additionally, an oxygen concentration control device is achieved by use of the air-fuel ratio controller. However, in an internal combustion engine having a system by which a secondary air is flowed into the upstream of the exhaust purifying catalyst according to another aspect of the present invention, the oxygen concentration control device may be achieved by a secondary air control device which controls the air-fuel ratio of the exhaust gas flowed into the exhaust purifying catalyst.

The decision of the degradation of the exhaust purifying catalyst is performed in this way so that the information about the hydrogen concentration level is detected by the technique of the first embodiment. It is therefore possible to perform the decision of the degradation of the exhaust purifying catalyst with a few detection error, which is caused by the temperature, the individual difference of the air-fuel ratio sensor, and the like, at low cost.

Further, the hydrogen detecting device according to the present invention is not limited to the use in the internal combustion engine abnormality deciding device. There is provided an internal combustion engine control device characterized by including: the hydrogen detecting device according to the present invention; a controller controlling the internal combustion engine on the basis of the information about the hydrogen concentration level detected by a detecting portion, the gas to be detected being the exhaust gas exhausted from the internal combustion engine. The air-fuel ratio controller may detect the hydrogen concentration level while performing the air-fuel ratio feedback control. However, the air-fuel ratio controller may temporarily stop the air-fuel ratio feedback control, and the target air-fuel ratio may be controlled in order to detect the hydrogen concentration level. The air-fuel ratio controller temporarily stops the air-fuel ratio feedback control and the hydrogen concentration level is detected in this manner, thereby allowing the detection of the hydrogen concentration level with accuracy. This achieves the fine control of the internal combustion engine.

Furthermore, the hydrogen detecting device according to the present invention is not limited to the use in the internal combustion engine. The device may include: a sensor detecting an oxygen concentration of a gas to be detected on the basis of oxygen partial pressure, and having an electromotive force with a Z characteristic in the vicinity of a reference oxygen concentration; and an oxygen concentration controller switching the oxygen concentration of the gas, to be detected, flowed into the sensor to high concentration or low concentration with respect to the oxygen concentration. The device is capable of measuring the high and low oxygen concentration response periods, thereby detecting the hydrogen concentration level.

The invention claimed is:

1. A hydrogen detecting method comprising:

obtaining a low oxygen concentration response period that is a response period from a time a target air-fuel ratio is switched from lean to rich to a time an output of a sensor detecting an oxygen concentration of an exhaust as is reflected by the switching with a feedback control stopped, the feedback control controlling the target air-fuel ratio of the exhaust gas on a basis of a detection result of the sensor such that an air-fuel ratio of the exhaust gas comes close to a theoretical air-fuel ratio;

obtaining a high oxygen concentration response period that is a response period from a time the target air-fuel ratio is switched from rich to lean to a time an output of the sensor is reflected by the switching with the feedback control stopped;

detecting an information according to a hydrogen concentration level on a basis of the high and low oxygen concentration response periods; and deciding that there is a variation between cylinders, when the hydrogen concentration level detected by the detecting is greater than or equal to a given value.

\* \* \* \* \*